United States Patent
Muto et al.

(10) Patent No.: US 7,547,716 B2
(45) Date of Patent: Jun. 16, 2009

(54) SULFONAMIDE DERIVATIVES

(75) Inventors: Susumu Muto, Tokyo (JP); Masayuki Komukai, Chiba (JP); Akiko Itai, Tokyo (JP)

(73) Assignee: Institute of Medicinal Molecular Design, Inc., Tokyo (JP)

( * ) Notice: Subject to any disclaimer, the term of this patent is extended or adjusted under 35 U.S.C. 154(b) by 50 days.

(21) Appl. No.: 10/478,687

(22) PCT Filed: Jun. 7, 2002

(86) PCT No.: PCT/JP02/05671

§ 371 (c)(1),
(2), (4) Date: May 24, 2004

(87) PCT Pub. No.: WO03/007931

PCT Pub. Date: Jan. 30, 2003

(65) Prior Publication Data

US 2004/0234622 A1 Nov. 25, 2004

(30) Foreign Application Priority Data

Jun. 8, 2001 (JP) ............... 2001-174066
Nov. 19, 2001 (JP) ............... 2001-353026

(51) Int. Cl.
*A61K 31/18* (2006.01)
*A61K 31/19* (2006.01)
*A61K 31/27* (2006.01)
*A61K 31/36* (2006.01)

(52) U.S. Cl. ............ 514/357; 514/394; 514/466; 514/471; 514/569; 514/603; 546/338; 548/309.7; 549/451; 549/495; 562/427; 564/82; 564/86

(58) Field of Classification Search .......... 564/86, 564/82; 514/603, 357, 394, 466, 471, 569; 562/427; 549/451, 495; 546/338; 548/309.7
See application file for complete search history.

(56) References Cited

U.S. PATENT DOCUMENTS

| 5,284,856 | A | 2/1994 | Naik et al. |
| 5,340,565 | A | 8/1994 | Pero |
| 5,378,715 | A | 1/1995 | Stein et al. |
| 6,150,394 | A | 11/2000 | Watanabe et al. |
| 6,284,923 | B1 * | 9/2001 | Medina et al. ............ 564/86 |

FOREIGN PATENT DOCUMENTS

| DE | 767 692 | * | 2/1954 |
| EP | 0007206 | | 1/1980 |
| EP | 0305008 | | 3/1989 |
| EP | 0366061 | | 5/1990 |
| EP | 0558258 | | 9/1993 |
| EP | 0950656 | | 10/1999 |
| JP | 60-126219 | | 7/1985 |
| JP | 6-9585 | | 1/1994 |
| JP | 2528451 | | 6/1996 |
| WO | WO 99/37609 A1 | * | 4/1999 |
| WO | 00/32577 | | 6/2000 |
| WO | 01/49289 | | 7/2001 |

OTHER PUBLICATIONS

Palajma et al., Chem. Abst. 126:89157 (1997).*
English Language Abstract JP 60-126219.
J. Biol. Chem., vol. 275, p. 5600-5605, 2000.
J. Biol. Chem., vol. 276, p. 17693-17698, 2001.
Jpn. J. Cancer Res., vol. 80, p. 83-88, 1989.
Invest. New Drugs, vol. 18, p. 95-107, 2000.
Cancer Res., vol. 60, p. 2108-2112, 2000.
Cancer Res., vol. 59, p. 4375-4382 1999.
J. Biol. Chem., vol. 275, p. 10342-10348.
Cancer Res., vol. 61, p. 1065-1072.
Biochem. Biophy. Res. Commun., vol. 219, p. 778-783 1996.
Acta. Pharmacol. Sin., vol. 21, p. 35-40, 2000.
English Language Abstract JP2528451.
Pavelic K., et al.: "Calmodulin antagonist W 13 prevents DNA repair after bleomycin treatment of human urological tumor cells growing on extracellular matrix", International Journal of Biochemistry, vol. 19, No. 11, pp. 1091-1095, (1987).
Kikuchi Y., et al.: "Enhancement of antineoplastic effects of cisplatin by calmodulin antagonists in nude mice bearing human avarian carcinoma", Cancer Research, vol. 47, No. 24, pp. 6459-6461, (1987), Abstract.

(Continued)

*Primary Examiner*—Peter G O'Sullivan
(74) *Attorney, Agent, or Firm*—Greenblum & Bernstein, P.L.C.

(57) ABSTRACT

A medicament for enhancing an effect of a cancer therapy based on a mode of action of DNA injury, which comprises as an active ingredient a compound represented by the general formula (I) or a physiologically acceptable salt thereof:

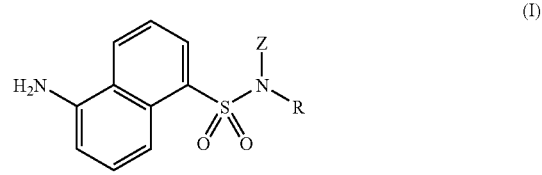

(I)

wherein R represents an aryl-substituted alkyl group, an heteroaryl-substituted alkyl group, a cycloalkyl-substituted alkyl group, or a cyclic hydrocarbon group wherein said cyclic hydrocarbon group may be saturated, partly saturated, or aromatic; or Z may bind to R to form a cyclic structure, Z represents a hydrogen atom or a $C_1$ to $C_6$ alkyl group. The medicament enhanced the effect of the cancer therapy and decreases a dose of an anticancer agent and/or radiation, and therefore, can reduce side effects resulting from the cancer therapy.

9 Claims, No Drawings

OTHER PUBLICATIONS

Kikuchi Y., et al.: "Effects of calmodulin antagonists on human ovarian cancer cell proliferation in vitro", Biochemical and Biophysical Research Communications, vol. 123, No. 1, pp. 385-392, (1984), Abstract.

Zhang Q., et al.: "Experiment of study of calmodulin antagonist, W-7, on the proliferation effect of human hepatocellular carcinoma", Chinese Pharmacological Bulletin, vol. 14, No. 5, pp. 463-466, (1998), Abstract.

Chemical Abstracts 1996:431588 of Palajma et al., SU 1648056 A3, Dec. 20, 1995.

* cited by examiner

SULFONAMIDE DERIVATIVES

FIELD OF INVENTION

The present invention relates to medicaments for enhancing the effect of cancer therapy on the basis of mechanism of inuring DNA, and novel compounds useful as active ingredients of said medicament.

BACKGROUND ART

Anticancer agents are administered in treatments of cancer patients at present. However, their life-prolongation rates are undesirably low, and moreover, cancer patients administered with an anticancer agent are forced to tolerate severe side effects such as fever, nausea, epilation, chill, fatigue, immune malfunction, gastrointestinal disorder, liver disorder, and kidney disorder, which becomes a cause of significant deterioration of the QOL (Quality of Life) of the cancer patients. Furthermore, reduction of sensitivity of cancer cells to anticancer agents, caused by the use of the anticancer agents, may lead to prolonged administration period of administration of the anticancer agents and increase of doses, and as a result, deaths resulting from side effects of the anticancer agents are often observed. Therefore, the administration of anticancer agents may spoil advantages of patients, as well as significantly diminish social and economic benefits. This is caused by the fact that anticancer agents, which are expectedly used to exhibit selective cytotoxicity to cancer cells that disorderly divide and proliferate, actually act cytotoxically on normal cells, particularly on cells in the intestine and marrow.

In recent years, reports have been made on caffeine which is a low molecule organic compound and UCN-01(7-hydroxy staurosporine) having actions to enhance radiation susceptibility of cancer cells which are radiation resistant (J. Biol. Chem., 275, 6600-6605, 2000; J. Biol. Chem., 276, 17693-17698, 2001). Cancer therapy by radiation is also based on the mode of action of artificial injury of DNAs, and is considered to be basically equivalent, to anticancer agents such as bleomycin based on the mode of action of DNA injury. Accordingly, it is believed that a drug that enhances selective toxicity to cancer cells can be developed even for anticancer agents based on the mode of action of DNA injury which are available at present.

In fact, it is reported that caffeine increases the actions of anticancer agents such as adriamycin, cisplatin, cyclophosphamide, and mitomycin C based on the mode of action of DNA injury (Jpn. J. Cancer. Res., 80, 83-88, 1989). However, potency remains insufficient, and separation from toxicity is unsatisfactory. UCN-01 is also reported to enhance actions of several kinds of anticancer agents based on the mode of action of DNA injury (Invest. New Drugs, 18, 95-107, 2000).

As for the mode of action of the potentiation of anticancer agents, the action is presumed to be based on a destruction of a certain part of the cell cycle (for example, G1 period and G2 period: Cancer Res., 60, 2108-2112, 2000; Cancer Res., 59, 4375-4882(1999), since caffeine and UCN-01 inhibit protein kinases involved in a control of a cell cycle (J. Biol. Chem., 275, 10342-10348, 2000; Cancer Res., 61, 1065-1072, 2001). However, no conclusive evidence has been obtained. In addition, since caffeine and UNC-01 as a staurosporin derivative have inhibitory actions against multiple kinds of protein kinases (Biochem. Biophys. Res. Commun., 219, 778-783, 1996; Acta Pharmacol. Sin., 21, 85-40, 2000), a possibility of involvement of a mechanism other than the destruction of the cell cycle can not be denied. Accordingly, a clear mode of action remains unidentified. Furthermore, there is a high possibility that these agents have inhibitory actions also against protein kinases participating in intracellular signal transduction, which is considered to be a possible cause of inducing serious side effects.

As explained above, no effective means is available at present to solve various problems caused by the cancer therapies based on the mode of action of DNA injury. Developments of new drugs or therapies, that potentiate the effects of available anticancer agents and radiation therapy based on the mode of action of DNA injury and that enhance selectivity to cancer cells to decrease side effects, will contribute to increase the QOL and advantages of cancer patients as well as social and economic benefits.

DISCLOSURE OF THE INVENTION

An object of the present invention is to provide medicaments for enhancing the effect of cancer therapy based on the mode of action of DNA injury. More specifically, an object of the present invention is to provide medicaments which, per se, have weak anticancer activity (cytotoxicity), but in combination of an anticancer agent based on the mode of action of DNA injury or a therapy such as radiation which gives artificial injuries to DNA, can selectively damage or kill cancer cells at a lower dose of anticancer agent or a lower radiation dose so as to significantly reduce affects on normal cells. Furthermore, another object of the present invention is to provide medicaments to reduce side effects resulting from cancer therapy by potentiation of the effects of the above cancer therapy and by reduction of a dose of the anticancer agent and/or radiation dose. Still further object of the present invention is to provide novel compounds which are useful as active ingredients of the above medicaments.

The inventors of the present invention focused on protein kinase inhibitors to solve the aforementioned objects, and carried out search for compounds having desired pharmacological activities by using computerized molecular design technology as a means to discover candidate compounds. The inventors carried out an automatic search program of a ligand from a three-dimensional compound database based on the three-dimensional structure of the protein by using the ATP binding regions of several kinds of protein kinases whose structures are registered in PDB (Protein Data Bank), and by virtual screenings, they selected compounds having potentials as protein kinase inhibitors from compounds registered in databases of commercial compounds. The inventors classified the resulting compounds on the basis of their skeletons, and by using several typical compounds, they carried out tests of combined effects with bleomycin on cancer cells and normal cells and tests of cytotoxicity to cancer cells and normal cells when the compounds are used alone. The inventors selected compounds having strong and desired pharmacological activities, and further prepared their derivatives to achieve the present invention.

The present invention thus provides a medicament for enhancing an effect of a cancer therapy based on a mode of action of DNA injury which comprises as an active ingredient a compound represented by the general formula (I) or a physiologically acceptable salt thereof:

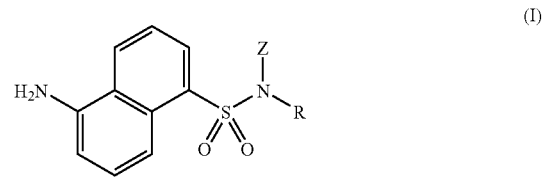

wherein R represents an aryl-substituted alkyl group which may be substituted, an heteroaryl-substituted alkyl group which may be substituted, a cycloalkyl-substituted alkyl group which may be substituted, or a cyclic hydrocarbon group which may be substituted (said cyclic hydrocarbon group may be saturated, partly saturated or aromatic); or Z may be bound to R to form a cyclic structure (the formed ring may be substituted), Z represents a hydrogen atom or a $C_1$ to $C_6$ alkyl group.

According to preferred embodiments of the present invention, provided are the aforementioned medicament wherein the cancer therapy based on the mode of action of DNA injury is carried out by administration of an anticancer agent and/or radiation; the aforementioned medicament wherein the anticancer agent is selected from a group consisting of bleomycin, adriamycin, cisplatin, cyclophosphamide, mitomycin C, and their derivatives; and the aforementioned medicament which is a specific inhibitor against a protein kinase and/or its analogous enzyme.

From another aspect, the present invention provides a medicament for reducing a side effect resulting from a cancer therapy based on the mode of action of DNA injury which comprises as an active ingredient a compound represented by the aforementioned general formula (I) or a physiologically acceptable salt thereof.

From further another aspect, the present Invention provides use of the compound represented by the aforementioned general formula (I) or the physiologically acceptable salt thereof for manufacture of the aforementioned medicament; a method of enhancing an effect of cancer therapy based on the mode of action of DNA injury in a mammal including a human, which comprises the step of applying a cancer therapy based on the mode of action of DNA injury to a cancer patient, and the step of administering the compound represented by the aforementioned general formula (I) or the physiologically acceptable salt thereof at a dose sufficient to potentiate the effect of the aforementioned cancer therapy; a method of reducing a side effect resulting from a cancer therapy based on the mode of action of DNA injury in a mammal including a human, which comprises the step of applying a cancer therapy based on the mode of action of DNA injury to a cancer patient, and the step of administering the compound represented by the aforementioned general formula (I) or the physiologically acceptable salt thereof at a dose sufficient to reduce the side effect of the aforementioned cancer therapy.

Furthermore, the present invention provides, a compound represented by the general formula (II) or a salt thereof.

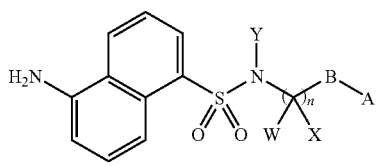

(II)

wherein A represents a $C_3$ to $C_6$ cycloalkyl group which may be substituted, a $C_6$ to $C_{10}$ aryl group which may be substituted, or a 4 to 10-membered monocyclic or bicyclic unsaturated, partly saturated or saturated heterocyclic group (said heterocyclic group may be substituted) which comprises 1 to 4 hetero atoms selected from the group consisting of nitrogen atom, oxygen atom, and sulfur atom; B represents a single bond or a methylene group which may be substituted; and W and X independently represent a hydrogen atom or a $C_1$ to $C_6$ alkyl group which may be substituted, or W may combine with a substituent of A to represent a $C_1$ to $C_4$ alkylene group (said alkylene group may be substituted); Y represents a hydrogen atom or a $C_1$ to $C_6$ alkyl group which may be substituted, or Y may combine with a substituent of A to represent a $C_1$ to $C_4$ alkylene group (said alkylene group may be substituted); and n represents 0 or 1.

Furthermore, the present invention provides a medicament comprising as an active ingredient a compound represented by the aforementioned general formula (II) or a physiologically acceptable salt thereof. This medicament can be used as a medicament to potentiate the effect of cancer therapy based on the mode of action of DNA injury. According to preferred embodiments of the present invention, provided are the aforementioned medicament wherein the cancer therapy based on the mode of action of DNA injury is carried out by the administration of an anticancer agent and/or radiation; the aforementioned medicament wherein the anticancer agent is selected from the group consisting of bleomycin, adriamycin, cisplatin, cyclophosphamide, mitomycin C, and their derivatives; and the aforementioned medicament which is a specific inhibitor of a protein kinase and/or analogous enzyme thereof.

From another aspect, the present invention provides a medicament which comprises the compound represented by the aforementioned general formula (II) or the physiologically acceptable salt thereof as an active ingredient, and which reduces a side effect resulting from a cancer therapy based on the mode of action of DNA injury.

From further another aspect, the present invention provides use of the compound represented by the aforementioned general formula (II) or the physiologically acceptable salt thereof for manufacture of the aforementioned medicament; a method of enhancing the effect of a cancer therapy based on the mode of action of DNA injury in a mammal including a human, which comprises the step of applying a cancer therapy based on the mode of action of DNA injury to a cancer patient and the step of administering the compound represented by the aforementioned general formula (II) or the physiologically acceptable salt thereof at a dose sufficient to potentiate the effect of the aforementioned cancer therapy; a method of reducing a side effect resulting from a cancer therapy based on the mode of action of DNA injury in a mammal including a human, which comprises the step of applying a cancer therapy based on the mode of action of DNA injury to a cancer patient and the step of administering the compound represented by the aforementioned general formula (II) or the physiologically acceptable salt thereof at a dose sufficient to potentiate the effect of the aforementioned cancer therapy.

BEST MODE FOR CARRYING OUT THE INVENTION

The terms used in the present specification have the following meanings.

The alkyl group may be straight chain, branched chain, cyclic, and combination of these unless otherwise specifically mentioned. More specifically, examples include methyl group, ethyl group, n-propyl group, isopropyl group, cyclopropyl group, n-butyl group, isobutyl group, sec-butyl group, tert-butyl group, cyclobutyl group, cyclopropylmethyl group, n-pentyl group, isopentyl group, neopentyl group, tert-pentyl group, cyclopentyl group, n-hexyl group, cyclohexyl group, 3,3-dimethylbutyl group, 2-ethylbutyl group, 2-methylpentyl group, 3-methylpentyl group, or 4-methylpentyl group. An alkyl moiety of other substituents containing the alkyl moiety have the same meaning. The alkylene group may either be a straight chain or a branched chain.

Where a cycloalkyl group is specifically referred to, for example, a 4 to 8-membered, particularly a 5 to 7-membered cycloalkyl group is preferred. The cycloalkyl group may either be monocyclic or polycyclic, however, a monocyclic cycloalkyl group is preferable. A cycloalkyl moiety of other substituents (for example, cycloalkyl-substituted alkyl group) containing the cycloalkyl moiety has the same meaning. In the cycloalkyl-substituted alkyl group, an alkyl moiety bonding to the cycloalkyl group is preferably either a straight chain or a branched chain, and preferred examples include a $C_1$ to $C_4$ alkyl group. Preferably, methyl group or ethyl group, and most preferably methyl group is used.

For the aryl group, any monocyclic or polycyclic aryl group may be used. For example, phenyl group, naphthyl group, or anthryl group may be suitably used, and it is more preferable to use phenyl group or naphthyl group. An aryl moiety of other substituents containing the aryl moiety (for example, aryl-substituted alkyl group) has the same meaning.

A type of a heteroatom contained as a ring-constituting atom in a heteroaryl group that constitutes a heteroaryl-substituted alkyl group is not particularly limited. The heteroatom may preferably be one or two or more heteroatoms selected from the group consisting of oxygen atom, nitrogen atom, and sulfur atom. An aromatic heterocycles that constitutes a heteroaryl group may either be monocyclic or polycyclic.

An alkyl moiety constituting an aryl-substituted alkyl group or a heteroaryl-substituted alkyl group may preferably be either a straight chain or a branched chain. For example, a $C_1$ to $C_4$ alkyl group may be suitably used. Preferably, methyl group or ethyl group, most preferably methyl group is used.

A cyclic hydrocarbon group may either be monocyclic or polycyclic. Furthermore, the cyclic hydrocarbon group may be saturated, partly saturated, or completely saturated. Examples include any of an aryl group or a cycloalkyl group, or a partly saturated aryl group (for example, 1,2,3,4-tetrahydro-1-naphthyl group). A cyclic structure formed by biding of Z to R may be either monocyclic or polycyclic. Preferably, the cyclic structure may be a polycyclic ring structure, more preferably, a bicyclic ring structure.

A type of a 4 to 10-membered monocyclic or bicyclic, and unsaturated, partly saturated, or completely saturated heterocyclic group is not particularly limited. Examples include thienyl group, furyl group, pyrrolyl group, oxazolyl group, isoxazolyl group, thiazolyl group, imidazolyl group, pyrazolyl group, benzothiophenyl group, benzofuranyl group, isobenzothiophenyl group, isobenzofuranyl group, indolyl group, isoindolyl group, indolizinyl group, 1H-indazolyl group, purinyl group, benzothiazolyl group, benzoxazolyl group, benzimidazolyl group, 1,2,3-thiadiazolyl group, 1,2,4-thiadiazolyl group, 1,8,4-thiadiazolyl group, 1,3,4-oxadiazolyl group, 1,2,3-triazolyl group, 1,2,4-triazolyl group, tetrazolyl group, chromenyl group, pyridyl group, pyridazinyl group, pyrimidinyl group, pyrazinyl group, quinolizinyl group, quinolyl group, isoquinolyl group, phthalazinyl group, naphthyridinyl group, quinoxalinyl group, quinazolinyl group, cinnolinyl group, pteridinyl group, 1,2,4-triazinyl group, chromanyl group, isochromanyl group, azetidinyl group, 2-oxoazetidinyl group, pyrrolidinyl group, pyrrolinyl group, imidazolidinyl group, imidazolinyl group, pyrazolidinyl group, pyrazolinyl group, piperidyl group, piperazinyl group, morpholino group, morpholinyl group, thiomorpholino group, thiomorpholinyl group, indolinyl group, isoindolinyl group, 1,2,3,4-tetrahydroquinolyl group, quinuclidinyl group, and methylenedioxyphenyl group.

In the present specification, when a certain functional group is defined as "which may be substituted", kinds, numbers, and positions of substituents existing in the functional groups are not particularly limited. Examples of these substituents include halogen atoms (any of fluorine atom, chlorine atom, bromine atom, or iodine atom is acceptable), hydroxy group, a $C_1$ to $C_6$ alkyl group, a $C_2$ to $C_6$ alkenyl group, a $C_2$ to $C_6$ alkynyl group, a $C_6$ to $C_{10}$ aryl group, a $C_7$ to $C_{12}$ aralkyl group, a $C_1$ to $C_8$ hydroxyalkyl group, trifluoromethoxy group, a $C_1$ to $C_6$ alkoxy group, a $C_2$ to $C_6$ alkenyloxy group, a $C_2$ to $C_6$ alkynyloxy group, a $C_6$ to $C_{10}$ aryloxy group, a $C_7$ to $C_{12}$ aralkyloxy group, a $C_1$ to $C_6$ hydroxyalkyloxy group, a $C_1$ to $C_6$ alkanoyl group, a $C_6$ to $C_{10}$ aroyl group, carboxy group, a $C_1$ to $C_6$ alkoxycarbonyl group, carbamoyl group, thiol group, a $C_1$ to $C_6$ alkylthio group, a $C_6$ to $C_{10}$ arylthio group, a $C_7$ to $C_{12}$ aralkylthio group, a $C_1$ to $C_6$ hydroxyalkylthio group, sulfonic acid group, a $C_1$ to $C_6$ alkylsulfonyl group, a $C_6$ to $C_{10}$ arylsulfonyl group, sulfamoyl group, formyl group, hydroxyimino group, a $C_1$ to $C_6$ alkoxyimino group, phenoxyimino group, cyano group, nitro group, amino group, formylamino group, a $C_1$ to $C_6$ alkanoylamino group, a $C_6$ to $C_{10}$ aroylamino group, a $C_1$ to $C_6$ alkoxycarbonylamino group, a $C_1$ to $C_6$ alkylsulfonylamino group, a $C_6$ to $C_{10}$ arylsulfonylamino group, amidino group, guanidino group, silyl group, stannyl group, and a heterocyclic group. These substituents may further be substituted with the aforementioned substituents. Examples include a halogenated alkyl group, a halogenated alkoxy group, a carboxy-substituted alkyl group, and an alkyl-substituted amino group. Furthermore, two or more substituents of the aforementioned substituents may form a ring together with the atoms to which they bind (carbon atom, nitrogen atom, boron atom, and the like). In these rings, one or more hetero atoms selected from the group consisting of nitrogen atom, oxygen atom, and sulfur atom may be included as ring-constituting atoms, and one or more substituents may exist on the ring. The ring may either be monocyclic or fused cyclic, or may be unsaturated, partly saturated, or completely saturated.

In the general formula (I), preferable examples of an aryl-substituted alkyl group represented by R include benzyl group, 1-phenethyl group, 2-phenethyl group, 2-phenylpropan-2-yl group, 1-naphthylmethyl group, 2-naphthylmethyl group, and 1-(1-naphthyl)ethyl group. When said aryl-substituted alkyl group has one or more substituents on the aryl ring, kinds of substituents, substituting positions, and numbers of the substituents are not limited. Examples of the substituents include halogen atoms (chlorine atom or fluorine atom), a $C_1$ to $C_4$ alkyl group, a $C_1$ to $C_4$ halogenated alkyl group (such as trifluoromethyl group), a $C_1$ to $C_4$ alkoxy group, phenyl group, a substituted phenyl group (such as tolyl group), methylenedioxy group, an aralkyl group (such as benzyl group), an aralkyloxy group (such as benzyloxy group), hydroxy group, nitro group, amino group, a substituted-amino group (such as dimethylamino group), sulfonamide group, a substituted-sulfonamide group, carboxyl group, an alkylsulfonyl group, or sulfamoyl group. However, the substituents on the aryl ring are not limited to those examples. One to three of these substituents may exist on the aryl ring, and when two or more substituents exist, they may be the same or different.

Examples of a heteroaryl group constituting a heteroaryl-substituted alkyl group represented by R include, but not limited thereto, pyridyl group, furyl group, thienyl group, benzimidazolyl group, and quinolyl group. An example of a cycloalkyl group constituting a cycloalkyl-substituted alkyl group represented by R includes cyclohexyl group. Examples of a cyclic hydrocarbon group represented by R include phenyl group, naphthyl group, indanyl group, 1,2,3,4-tetrahydro-1-naphthyl group, and cyclohexyl group. Examples of a ring formed by Z binding to R include 1,3-dihydro-2-isoindolyl group, and 1,2,3,4-tetrahydroisoquinolynyl group. The compounds wherein R is, benzyl group are particularly preferable. Z may preferably be a hydrogen atom.

The compounds represented by the general formula (I) may form salts. Kinds of salts are not particularly limited. When acidic groups exist, examples include metal salts such as lithium salt, sodium salt, potassium salt, magnesium salt, and calcium salt, or ammonium salts such as ammonium-salt, methylammonium salt, dimethylammonium salt, trimethylammonium salt, and dicyclohexylammonium salt, and when basic groups exist, examples include mineral acid salts such as hydrochloride, hydrobromide, sulfate, nitrate, and phosphate, or organic acid salts such as methane sulfonate, benzene sulfonate, para-toluene sulfonate, acetate, propionate, tartrate, fumarate, maleate, malate, oxalate, succinate, citrate, benzoate, mandelate, cinnamate, and lactate. Salts may sometimes be formed with amino acids such as glycine. As active ingredients of the medicaments of the present invention, pharmacologically acceptable salts are suitable.

The compounds or salts thereof represented by the general formula (I) may exist as hydrates or solvates. Furthermore, the compounds represented by the general formula (I) may sometimes have one or more asymmetric carbons, and may exist as stereoisomers such as optically active isomers and diastereomers. As active ingredients of the medicaments of the present invention, a pure form of a stereoisomer, any mixture of enantiomers or diastereomers, a racemate or the like may be used.

Furthermore, when the compounds represented by the general formula (I) have an olefinic double bond, its configuration may be in either E or Z. As an active ingredient of the medicament of the present invention, a geometrical isomer in either of the configurations or a mixture thereof may be used.

Examples of a class of compounds suitable as the active ingredients of the medicaments of the present invention include the compounds represented by the general formula (II). The compounds represented by the general formula (II) may form salts, and examples include those salts exemplified for the compounds represented by the general formula (I). The compounds or salts thereof represented by the general formula (II) may exist as hydrates or solvates. Any of these substances fall within the scope of the present invention. Furthermore, the compounds represented by the general formula (II) may sometimes have one or more asymmetric carbon atoms, and may exist as stereoisomers such as optically active isomers and diastereomers. A pure form of the stereoisomer, any mixture of the enantiomers or diastereomers, a racemate and the like all fall within the scope of the present invention. Furthermore, when the compounds represented by the general formula (II) have an olefinic double bond, its configuration may be in either E or Z. A geometrical isomer in either of the configurations or a mixture thereof falls within the scope of the present invention.

In the compounds represented by the general formula (II), n may preferably be 1. When n is 0, it is preferable that B is a single bond and A is an aryl group. In the compounds represented by the general formula (II), examples of the moiety represented by —(C(W)(X))$_n$—B-A are similar to those explained for R in the above general formula (I).

Examples of the compounds included in the general formula (II) are shown in the following. However, the compounds of the present invention are not limited to the following compounds.

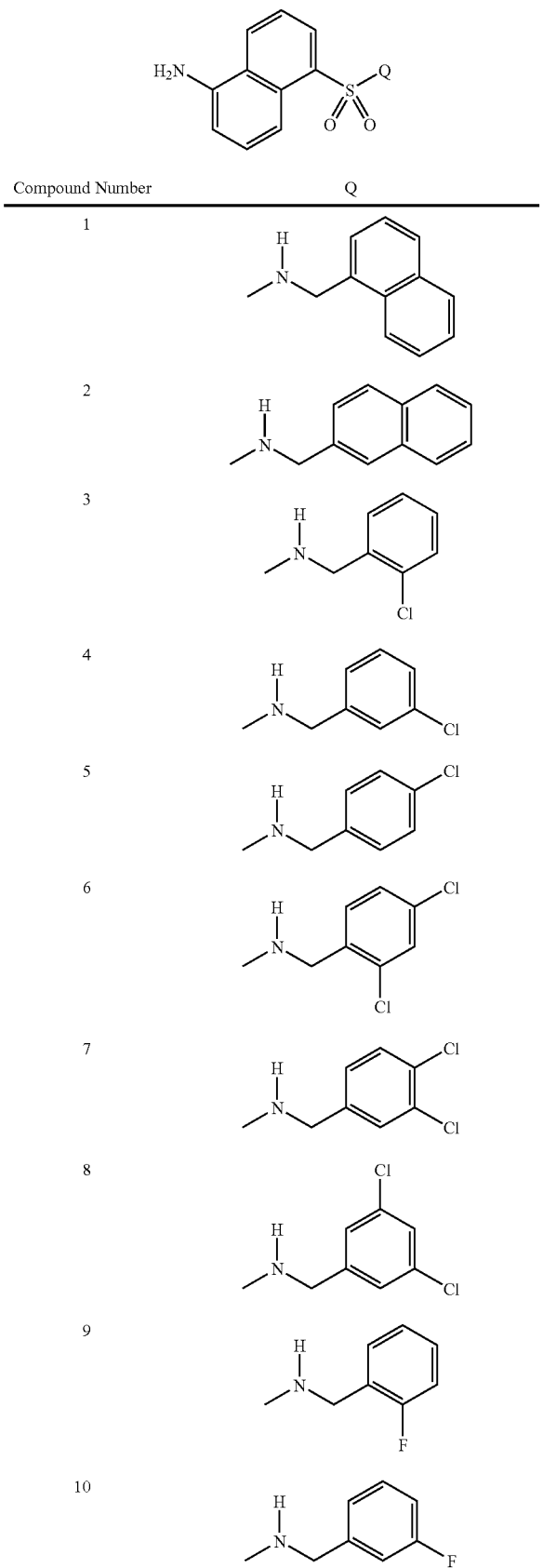

-continued

![Structure: 5-amino-naphthalene-1-sulfonyl-Q]

| Compound Number | Q |
|---|---|
| 11 | N-methyl-(4-fluorobenzyl)amine |
| 12 | N-methyl-(2,6-difluorobenzyl)amine |
| 13 | N-methyl-(3,4-difluorobenzyl)amine |
| 14 | N-methyl-(3,5-difluorobenzyl)amine |
| 15 | N-methyl-(2-methylbenzyl)amine |
| 16 | N-methyl-(3-methylbenzyl)amine |
| 17 | N-methyl-(4-methylbenzyl)amine |
| 18 | N-methyl-(4-tert-butylbenzyl)amine |
| 19 | N-methyl-(2-trifluoromethylbenzyl)amine |
| 20 | N-methyl-(3-trifluoromethylbenzyl)amine |

-continued

![Structure: 5-amino-naphthalene-1-sulfonyl-Q]

| Compound Number | Q |
|---|---|
| 21 | N-methyl-(4-trifluoromethylbenzyl)amine |
| 22 | N-methyl-(4-biphenyl)methylamine |
| 23 | N-methyl-(2-(4-methylphenyl)benzyl)amine |
| 24 | N-methyl-(2-methoxybenzyl)amine |
| 25 | N-methyl-(3-methoxybenzyl)amine |
| 26 | N-methyl-(4-methoxybenzyl)amine |
| 27 | N-methyl-(benzo[d][1,3]dioxol-5-ylmethyl)amine |
| 28 | N-methyl-(2,3-dimethoxybenzyl)amine |
| 29 | N-methyl-(2,4-dimethoxybenzyl)amine |

-continued

![Structure: 5-amino-naphthalene-1-sulfonyl-Q]

| Compound Number | Q |
|---|---|
| 30 | -NH-CH2-C6H3(3,4-diOMe) |
| 31 | -NH-CH2-C6H3(3,5-diOMe) |
| 32 | -NH-CH2-C6H2(2,4,6-triOMe) |
| 33 | -NH-CH2-C6H2(3,4,5-triOMe) |
| 34 | -NH-CH2-C6H4(2-OEt) |
| 35 | -NH-CH2-C6H4(3-OBn) |
| 36 | -NH-CH2-C6H4(4-OBn) |
| 37 | -NH-CH2-(6-methoxynaphth-2-yl) |
| 38 | -NH-CH2-C6H4(3-OH) |

-continued

![Structure: 5-amino-naphthalene-1-sulfonyl-Q]

| Compound Number | Q |
|---|---|
| 39 | -NH-CH2-C6H3(3,4-diOH) |
| 40 | -NH-CH2-C6H3(3-OMe,4-OH) |
| 41 | -NH-CH2-C6H4(3-NO2) |
| 42 | -NH-CH2-C6H4(4-NO2) |
| 43 | -NH-CH2-C6H4(2-NH2) |
| 44 | -NH-CH2-C6H4(3-NH2) |
| 45 | -NH-CH2-C6H4(4-NH2) |
| 46 | -NH-CH2-C6H4(3-NHSO2Me) |
| 47 | -NH-CH2-C6H4(4-NMe2) |
| 48 | -NH-CH2-C6H4(4-COOH) |
| 49 | -NH-CH2-C6H4(4-SO2Me) |

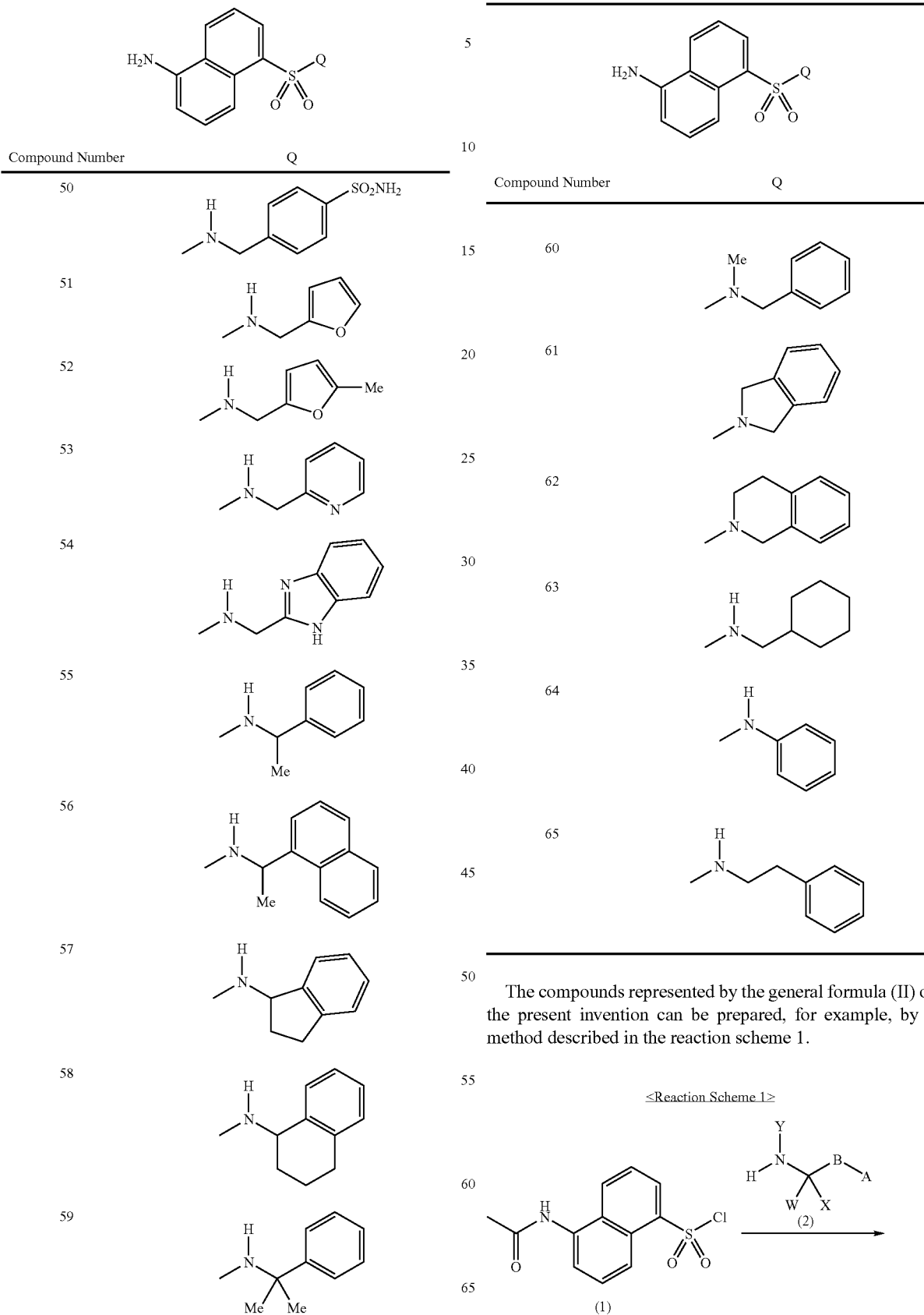
The compounds represented by the general formula (II) of the present invention can be prepared, for example, by a method described in the reaction scheme 1.

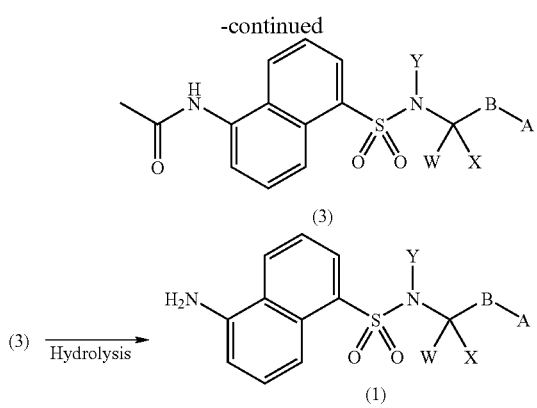

As for 5-(acetylamino)-1-naphthalenesulfonyl chloride (1), methods for preparation of the compound are already disclosed in the U.S. Pat. No. 5,378,715 and the Japanese Patent No.2628451. As for the amine (2) wherein A, B, W, X, and Y have the same meanings as those defined in the general formula (II), most of the amines in the free form or acid addition salts are widely available in the market, and the commercial products can be obtained and directly used. Furthermore, the amine (2) wherein A, B, W, X, and Y have the same meanings as those defined in the general formula (II) can also be prepared by methods readily understandable by those skilled in the art (for example, reduction of a corresponding nitro compound, reduction of a cyano compound, reduction of a carbamoyl compound and the like), and it is also understandable that the resulting amine can be used for preparation of the compounds of the present invention.

By reacting 5-(acetylamino)-1-naphthalenesulfonyl chloride (1) with the amine (2) wherein A, B, W, X, and Y have the same meanings as those defined in the general formula (II), the compound of the formula (3) wherein A, B, W, X, and Y have the same meanings as those defined in the general formula (II) can be obtained. This reaction is carried out in the presence or absence of a base and/or a catalyst, with or without a solvent, at a reaction temperature of −30° C. to a refluxing temperature of a solvent used.

Examples of the bases include inorganic bases such as sodium hydroxide, potassium hydroxide, sodium carbonate, potassium carbonate, and sodium hydrogencarbonate, or organic bases such as pyridine, triethylamine, ethyldiisopropylamine, and N,N-diethylaniline. Examples of the catalysts include 4-dimethylaminopyridine and tetrabutylammoniumbromide. Any solvent can be used as long as it does not inhibit the reaction, and examples include ethyl acetate, dichloromethane, dichloroethane, chloroform, tetrahydrofuran, 1,2-dimethoxyethane, 1,4-dioxane, benzene, toluene, monochlorobenzene, 1,2-dichlorobenzene, N,N-dimethylformamide, N-methylpyrrolidone, methanol, ethanol, 1-propanol, 2-propanol, acetone, 2-butanone, and water. These solvents can be used alone or as a mixture, or as two phase solvents.

The acetyl group of the resulting compound of the formula (8) wherein A, B, W, X, and Y have the same meanings as those defined in the general formula (II) is then hydrolyzed to prepare the compounds represented by the general formula (II). This reaction is carried out in the presence of an acid or a base, with or without a solvent, at a reaction temperature of from −0° C. to a refluxing temperature of a solvent.

Examples of the acids include mineral acids such as hydrochloric acid and sulfuric acid, and Lewis acids such as triethyloxonium tetrafluoroborate. Examples of the bases include inorganic bases such as sodium hydroxide, potassium hydroxide, and metallic sodium, or organic bases such as hydrazine. Any solvent can be used as long as it does not inhibit the reaction. Examples include tetrahydrofuran, 1,2-dimethoxyethane, 1,4-dioxane, methanol, ethanol, 1-propanol, 2-propanol, water, and acetic acid, and these solvents can be used alone or as a mixed solvent.

Examples of preparation methods of the salts of the compounds represented by the general formula (II) include a direct preparation of salts by a hydrolysis of the acetyl group of the compounds of the aforementioned formula (8) wherein A, B, W, X, and Y have the same meanings as those defined in the general formula (II), and a preparation wherein the free form of the compounds represented by the general formula (II) is first prepared by the above hydrolysis, and then the free form is converted to salts. These methods are easily understood by those skilled in the art.

In the examples of the specification, methods for preparation of typical compounds falling within the general formula (II) are explained in detail. Accordingly, those skilled in the art can prepare any compound encompassed within the general formula (II) by referring to the general explanations of the aforementioned preparation methods and specific explanations of the preparation methods of the examples, and by choosing appropriate starting materials, reagents, and reaction conditions and by adding appropriate modification and alteration to these methods, if necessary.

Medicaments of the present invention can be used to enhance the effect of cancer therapy based on the mode of action of DNA injury, including cancer chemotherapies by using anticancer agents and radiation therapies of cancer that induce DNA injury. Typical examples of anticancer agents that induces DNA injury include bleomycin, adriamycin, cisplatin, cyclophosphamide, and mitomycin C. Besides these derivatives, any of anticancer agents involving the mode of action of DNA injury can be targets of the medicaments of the present invention. The medicaments of the present invention may be used where either of a cancer chemotherapy using anticancer agents or a radiation therapy of cancer that induce DNA injury is solely carried out, or in a cancer therapy where a combination of these therapies is carried out.

Although it is not intended to be bound by any specific theory, the medicament of the present invention can bind to a protein kinase or its analogous enzyme that is activated after DNA injury, and terminate the functions of the enzyme to kill cancer cells. As a result, the medicaments can enhance the effect of the cancer therapy and can lower a dose of the anticancer agent and/or radiation for the cancer therapy, thereby reduce side effects resulting from the cancer therapy.

As the active ingredient of the medicament of the present invention, a hydrate or a solvate of the compounds represented by the aforementioned general formulas (I) or (II) or physiologically acceptable salts thereof may be used. Furthermore, when the compound contains one or more asymmetric carbon atoms, any of a pure form of optically active compound or any mixture of optically active compounds, or a racemate may be used. As the active ingredient of the medicament of the present invention, one or more kinds of substances selected from the group consisting of the aforementioned compound and a physiologically acceptable salt thereof, and a hydrate thereof and a solvate thereof may be used.

As the medicament of the present invention, the aforementioned substance, per se, may be administered. Preferably, the medicament may be administered as a pharmaceutical composition for oral or parenteral administration that may be prepared by methods well known to those skilled in the art. Examples of pharmaceutical compositions suitable for oral administration include tablets, capsules, powders, subtilized granules, granules, solution, and syrup, and examples of pharmaceutical compositions suitable for parenteral administration include Injections, suppositories, inhalants, instillations, nasal drops, ointments, percutaneous absorbents, transmucosal absorptions, cream, and plaster.

The aforementioned pharmaceutical compositions can be prepared by adding pharmacologically and pharmaceutically acceptable additives. Examples of pharmacologically and pharmaceutically acceptable additives include excipients, disintegrators or disintegration aids, binders, lubricants, coating agents, colorants, diluents, base materials, dissolving aids or dissolution adjuvants, isotonizing agents, pH modifiers, stabilizers, propellants, and adhesives. One or more kinds of anticancer agents based on the mode of action of DNA injury may be added to the aforementioned pharmaceutical compositions.

A dose of the medicament of the present invention is not particularly limited. The dose may be selected appropriately depending on a kind of the active ingredient and a kind of a cancer therapy. Further, the dose may be appropriately increased or decreased depending on various factors that should be generally considered such as the weight and age of a patient, a kind and symptom of a disorder, and an administration route. Generally, for an oral administration, the medicament may be used in a range of 0.01 to 1,000 mg for an adult per day.

EXAMPLES

The present invention will be explained more specifically with reference to the following examples. However the scope of the present invention is not limited to the following examples.

Example 1

Preparation of 5-amino-N-[(1-naphthalenyl)methyl]-1-naphthalenesulfonamide hydrochloride (Compound No, 1)

(1) Preparation of N-[5-[[[(1-naphthalenyl)methyl]amino]sulfonyl]-1-naphthalenyl]acetamide.

1-Naphthylmethylamine (174 mg, 1.1 mmol) was dissolved in tetrahydrofuran (10 ml), and 5-(acetylamino)-1-naphthalenesulfonyl chloride (284 mg, 1 mmol) was added under ice cooling and stirring. Then, triethylamine (0.17 mL, 1.2 mmol) was added and the mixture was stirred at room temperature for 1 hour. The reaction mixture was poured into diluted hydrochloric acid and extracted with ethyl acetate. The ethyl acetate layer was washed successively with aqueous sodium hydrogen carbonate, water, and saturated brine, and after the layer was dried over anhydrous sodium sulfate, the residue obtained by evaporation of the solvent under reduced pressure was crystallized by a mixed solvent of ethyl acetate/diisopropyl ether to give the title compound as a light brown crystal (325 mg, 80.4%).

$^1$H-NMR(DMSO-$d_6$, δ): 2.21(3H, s), 4.45(2H, d, J=5.7 Hz), 7.73-7.41(3H, m), 7.44-7.49(1H, m), 7.65(2H, dd, J=8.1, 7.8 Hz), 7.76(1H, d, J=7.5 Hz), 7.80(1H, d, J=7.5 Hz), 7.87-7.91(2H, m), 8.20(1H, dd, J=7.5, 0.9 Hz), 8.35(1H, d, J=8.7 Hz), 8.54-8.57(2H, m), 10.09(1H, s).

(2) Preparation of 5-amino-N-[(1-naphthalenyl)methyl]-1-naphthalenesulfonamide hydrochloride.

N-[5-[[[(1-naphthalenyl)methyl]amino]sulfonyl]-1-naphthalenyl]acetamide (226 mg, 0.56 mmol) was suspended in a mixed solution of 1-propanol (8 ml), concentrated hydrochloric acid (1 ml) and water (1 ml), and the mixture was refluxed for 1 hour. The crystal precipitated by cooling of the reaction mixture to room temperature was filtered and washed with the mixed solvent of 1-propanol/diisopropyl ether under reflux to give the title compound an a white crystal (201 mg, 90.8%).

$^1$H-NMR(DMSO-$d_6$, δ): 4.33-4.44(2H, m), 7.09-7.21(1H, m), 7.88-7.41(3H, m), 7.45-7.50(2H, m), 7.54-7.61(1H, m), 7.80(1H, dd, J=8.1, 1.8 Hz), 7.87-7.98(2H, m), 8.15(1H, d, J=7.2 Hz), 8.35(1H, d, J=8.7 Hz), 8.42-8.51(1H, m).

The compounds from Example 2 to Example 66 were prepared in the same manner as the method of Example 1. The yield and the physical properties data are described below. Details of preparation are also described for examples carried out under different conditions.

Example 2

Preparation of 5-amino-N-[(2-naphthalenyl)methyl]-1-naphthalenesulfonamide hydrochloride (Compound No. 2)

(1) Preparation of N-[5-[[[(2-naphthalenyl)methyl]amino]sulfonyl]-1-naphthalenyl]acetamide.

Yield: 76%

$^1$H-NMR(DMSO-$d_6$, δ): 2.20(3H, s), 4.21(2H, d, J=6.0 Hz), 7.29(1H, dd, J=8.4, 1.5 Hz), 7.45(2H, dt, J=9.3, 3.3 Hz), 7.61(2H, dd, J=8.4, 7.5 Hz), 7.73(4H, m), 8.17(1H, d, J=6.6 Hz), 8.31(1H, d, J=8.4 Hz), 8.58(1H, d, J=8.4 Hz), 8.65(1H, t, J=6.0 Hz), 10.05(1H, s).

(2) Preparation of 5-amino-N-[(2-naphthalenyl)methyl]-1-naphthalenesulfonamide hydrochloride.

Yield: 92%

$^1$H-NMR(DMSO-$d_6$, δ): 4.12(2H, d, J=6.0 Hz), 7.29(1H, dd, J=8.4, 1.8 Hz), 7.45(3H, m), 7.66(3H, m), 7.72(1H, m), 7.75(1H, d, J=8.4 Hz), 7.88(1H, m), 8.18(1H, dd, J=7.5, 0.9 Hz), 8.35(1H, d, J=8.4 Hz), 8.40(1H, d, J=8.7 Hz), 8.66(1H, t, J=6.0 Hz).

Example 3

Preparation of 5-amino-N-[(2-chlorophenyl)methyl]-1-naphthalenesulfonamide hydrochloride (Compound No. 3)

(1) Preparation of N-[5-[[[(2-chlorophenyl)methyl]amino]sulfonyl]-1-naphthalenyl]acetamide.

Yield: 74.2%

$^1$H-NMR(DMSO-$d_6$, δ): 2.20(3H, s), 4.13(2H, s), 7.13-7.23(2H, m), 7.28-7.37(2H, m), 7.61-7.71(2H, m), 7.76(1H, d, J=7.2 Hz), 8.14(1H, dd, J=7.5, 1.2 Hz), 8.32(1H, d, J=8.4 Hz), 8.52(1H, d, J=8.7 Hz), 8.60(1H, s), 10.07(1H, s).

(2) Preparation of 5-amino-N-[(2-chlorophenyl)methyl]-1-naphthalenesulfonamide hydrochloride.

Yield: 79.1%

$^1$H-NMR(DMSO-$d_6$, δ): 4.11(2H, d, J=6.0 Hz), 7.14-7.23 (2H, m), 7.28-7.31(1H, m), 7.34-7.37(2H, m), 7.56-7.65(2H, m), 8.14(1H, d, J=8.1 Hz), 8.32(2H, t, J=8.4 Hz), 8.61(1H, t, J=6.0 Hz).

Example 4

Preparation of 5-amino-N-[(3-chlorophenyl)methyl]-1-naphthalenesulfonamide hydrochloride (Compound No. 4)

(1) Preparation of N-(5-[[[(3-chlorophenyl)methyl]amino]sulfonyl]-1-naphthalenyl]acetamide.

Yield: 71.6%

$^1$H-NMR(DMSO-$d_6$, δ): 2.20(3H, s), 4.06(2H, d, J=6.3 Hz), 7.07-7.12(1H, m), 7.18-7.20(2H, m), 7.60-7.71(2H, m), 7.76(1H, d, J=7.2 Hz), 8.13(1H, dd, J=7.2, 1.2 Hz), 8.33(1H, d, J=8.7 Hz), 8.50(1H, d, J=8.4 Hz), 8.62(1H, d, J=6.8 Hz), 10.06(1H, s).

(2) Preparation of 5-amino-N-[(3-chlorophenyl)methyl]-1-naphthalenesulfonamide hydrochloride.

Yield: 82.8%

$^1$H-NMR(DMSO-$d_6$, δ): 4.05(2H, d, J=6.3 Hz), 7.06-7.11(1H, m), 7.15-7.21(3H, m), 7.43(1H, d, J=7.5 Hz), 7.56-7.67(2H, m), 8.14(1H, d, J=8.4 Hz), 8.34(2H, d, J=8.7 Hz), 8.64(1H, t, J=6.3 Hz).

Example 5

Preparation of 5-amino-N-[(4-chlorophenyl)methyl]-1-naphthalenesulfonamide hydrochloride (Compound No. 5)

(1) Preparation of N-[5-[[[(4-chlorophenyl)methyl]amino]sulfonyl]-1-naphthalenyl]acetamide.

Yield: 72.9%

$^1$H-NMR(DMSO-$d_6$, δ): 2.20(3H s), 4.02(2H, d, J=6.0 Hz), 7.17(2H, d, J=8.4 Hz), 7.25(2H, d, J=8.7 Hz), 7.61-7.71(2H, m), 7.77(1H, d, J=7.5 Hz), 8.13(1H, dd, J=7.5, 1.2 Hz), 8.34(1H, d, J=9.0 Hz), 8.50(1H, d, J=8.4 Hz), 8.59(1H, t, J=6.0 Hz), 10.08(1H, s).

(2) 5-Amino-N-[(4-chlorophenyl)methyl]-1-naphthalenesulfonamide hydrochloride.

Yield: 77.8%

$^1$H-NMR(DMSO-$d_6$, δ): 4.01(2H, d, J=6.0 Hz), 7.18(2H, d, J=8.4 Hz), 7.26(2H, d, J=8.4 Hz), 7.38(1H, d, J=7.5 Hz), 7.59(1H, t, J=8.4 Hz), 7.64(1H, t, J=8.4 Hz), 8.12(1H, d, J=7.5 Hz), 8.30(1H, d, J=8.4 Hz), 8.35(1H, d, J=8.4 Hz), 8.58(1H, t, J=6.3 Hz).

Example 6

Preparation of 5-amino-N-[(2,4-dichlorophenyl)methyl]-1-naphthalenesulfonamide hydrochloride (Compound No. 6)

(1) Preparation of N-[5-[[[(2,4-dichlorophenyl)methyl]amino]sulfonyl-1-naphthalenyl]acetamide.

Yield: 76.5%

$^1$H-NMR(DMSO-$d_6$, δ): 2.20(3H, s), 4.10(2H, s), 7.26(1H, dd, J=8.4, 1.2 Hz), 7.36(1H, d, J=8.7 Hz), 7.44(1H, d, J=2.1 Hz), 7.60-7.71(2H, m), 7.78(1H, d, J=7.5 Hz), 8.12(1H, dd, J=7.5, 1.2 Hz), 8.34(1H, d, J=8.4 Hz), 8.49(1H, d, J=8.4 Hz), 8.66(1H, 9), 10.07(1H, s).

(2) Preparation of 5-amino-N-[(2,4-dichlorophenyl)methyl]-1-naphthalenesulfonamide hydrochloride.

Yield: 70.4%

$^1$H-NMR(DMSO-$d_6$, δ): 4.08(2H, d, J=6.0 Hz), 7.25-7.29(2H, m), 7.37(1H, d, J=8.4 Hz), 7.45(1H, d, J=1.8 Hz), 7.55(1H, t, J=8.4 Hz), 7.59(1H, t, J=8.4 Hz), 8.10(1H, d, J=7.2 Hz), 8.20(1H, d, J=8.7 Hz), 8.35(1H, d, J=9.0 Hz), 8.62(1H, t, J=6.0 Hz).

Example 7

Preparation of 5-amino-N-[(3,4-dichlorophenyl)methyl]-1-naphthalenesulfonamide hydrochloride (Compound No. 7)

(1) Preparation of N-6-[[[(3,4-dichlorophenyl)methyl]amino]sulfonyl]-1-naphthalenyl]acetamide.

Yield: 71.1%

$^1$H-NMR(DMSO-$d_6$, δ): 2.20(3H, s), 4.06(1H, d, J=6.0 Hz), 7.11(1H, dd, J=8.4, 2.1 Hz), 7.32(1H, d, J=1.5 Hz), 7.41(1H, d, J=8.4 Hz), 7.56-7.71(2H, m), 7.78(1H, d, J=7.5 Hz), 8.12(1H, d, J=6.3 Hz), 8.34(1H, d, J=8.7 Hz), 8.48(1H, d, J=8.7 Hz), 8.64(1H, t, J=6.0 Hz), 10.05(1H, s).

(2) Preparation of 5-amino-N-[(3,4-dichlorophenyl)methyl]-1-naphthalenesulfonamide hydrochloride.

Yield: 87.8%

$^1$H-NMR(DMSO-$d_6$, δ): 4.04(2H, d, J=6.6 Hz), 7.11(1H, dd, J=8.4, 1.2 Hz), 7.33(1H, d, J=2.1 Hz), 7.36(1H, d, J=7.5 Hz), 7.42(1H, d, J=8.4 Hz), 7.57-7.65(2H, m), 8.12(1H, d, J=7.5 Hz), 8.27(1H, d, J=8.4 Hz), 8.35(1H, d, J=8.4 Hz), 8.64(1H, t, J=6.3 Hz).

Example 8

Preparation of 5-amino-N-[(3,5-dichlorophenyl)methyl]-1-naphthalenesulfonamide hydrochloride (Compound No. 8)

(1) Preparation of N-[5-[[[(3,5-dichlorophenyl)methyl]amino]sulfonyl]-1-naphthalenyl]acetamide.

Yield: 77%

$^1$H-NMR(DMSO-$d_6$, δ): 2.20(3H, s), 4.08(2H, d, J=6.3 Hz), 7.12(2H, d, J=1.8 Hz), 7.31(1H, dd, J=1.8, 1.5 Hz), 7.63(1H, dd, J=8.4, 7.5 Hz), 7.69(1H, dd, J=8.4, 7.5 Hz), 7.77(1H, d, J=7.2 Hz), 8.12(1H, dd, J=7.2, 0.9 Hz), 8.33(1H, d, J=8.4 Hz), 8.47(1H, d, J=8.4 Hz), 8.67(1H, t, J=6.3 Hz), 10.05(1H, s).

(2) Preparation of 5-amino-N-[(3,5-dichlorophenyl)methyl]-1-naphthalenesulfonamide hydrochloride.

Yield: 90%

$^1$H-NMR(DMSO-$d_6$, δ): 4.07(2H, d, J=6.3 Hz), 7.12(2H, d, J=1.5 Hz), 7.32(1H, dd, 0J=1.8, 1.5 Hz), 7.37(1H, d, J=7.5 Hz), 7.61(2H, ddd, J=8.4, 7.5, 2.1 Hz), 8.12(1H, d, J=7.2 Hz), 8.27(1H, d, J=8.7 Hz), 8.84(1H, d, J=8.4 Hz), 8.68(1H, t, J=6.3 Hz).

Example 9

Preparation of 5-amino-N-[(2-fluorophenyl)methyl-1-naphthalenesulfonamide hydrochloride (Compound No. 9)

(1) Preparation of N-[5-[[[(2-fluorophenyl)methyl]amino]sulfonyl]-1-naphthalenyl]acetamide.

Yield: 75%

$^1$H-NMR(DMSO-$d_6$, δ): 2.20(3H, s), 4.09(2H, d, J=6.0 Hz), 7.00(2H, m), 7.21(2H, m), 7.62(1H, dd, J=8.4, 7.5 Hz), 7.66(1H, dd, J=8.1, 7.8 Hz), 7.75(1H, d, J=7.5 Hz), 8.13(1H, dd, J=7.5, 0.9 Hz), 8.32(1H, d, J=8.4 Hz), 8.50(1H, d, J=8.4 Hz), 8.56(1H, t, J=6.0 Hz), 10.05(1H, s).

(2) Preparation of 05-amino-N-[(2-fluorophenyl)methyl]-1-naphthalenesulfonamide hydrochloride.
Yield: 69%
$^1$H-NMR(DMSO-d$_6$, δ): 4.08(2H, d, J=6.0 Hz), 6.97(1H, d, J=8.1 Hz), 7.00(1H, m), 7.21(2H, m), 7.44(1H, d, J=7.5 Hz), 7.61(1H, dd, J=8.4, 7.8 Hz), 7.64(1H, dd, J=8.7, 7.5 Hz), 8.14(1H, dd, J=7.2, 0.6 Hz), 8.33(1H, d, J=8.1 Hz), 8.36(1H, d, J=8.1 Hz), 8.58(1H, t, J=6.0 Hz).

Example 10

Preparation of 5-amino-N-[(3-fluorophenyl)methyl]-1-naphthalenesulfonamide hydrochloride (Compound No. 10)

(1) Preparation of N-(5-[[[(3-fluorophenyl)methyl]amino]sulfonyl)-1-naphthalenyl]acetamide.
Yield: 77.2%
$^1$H-NMR(DMSO-d$_6$, δ): 2.20(3H, s), 4.06(2H, d, J=6.3 Hz), 6.94-6.99(3H, m), 7.17-7.25(1H, m), 7.63(1H, dd, J=8.4, 7.2 Hz), 7.66-7.71(1H, m), 7.76(1H, d, J=6.9 Hz), 8.13(1H, dd, J=8.4, 1.2 Hz), 8.33(1H, d, J=8.4 Hz), 8.51(1H, d, J=8.4 Hz), 8.61(1H, t, J=6.3 Hz), 10.06(1H, s).

(2) Preparation of 5-amino-N-[(3-fluorophenyl)methyl]-1-naphthalenesulfonamide hydrochloride
Yield: 86.3%
$^1$H-NMR(CD$_3$OD, δ): 4.14(2H, s), 6.73-3.84(3H, m), 7.03-7.10(1H, m), 7.70-7.80(3H, m), 8.18(1H, dt, J=8.7, 0.9 Hz), 8.32(1H, dd, J=7.5, 1.2 Hz), 8.82(1H, dt, J=8.7, 0.9 Hz).

Example 11

Preparation of 5-amino-N-[(4-fluorophenyl)methyl]-1-naphthalenesulfonamide hydrochloride (Compound No. 11)

(1) Preparation of N-(5-[[[(4-fluorophenyl)methyl]amino]sulfonyl]-1-naphthalenyl]acetamide.
Yield: 78.7%
$^1$H-NMR(DMSO-d$_6$, δ): 2.20(3H, s), 4.01(2H, d, J=6.0 Hz), 6.96-7.04(2H, m), 7.14-7.21(2H, m), 7.63(1H, dd, J=8.4, 7.5 Hz), 7.67(1H, t, J=8.4 Hz), 7.76(1H, d, J=7.5 Hz), 8.12(1H, dd, J=7.5, 1.2 Hz), 8.33(1H, d, J=8.7 Hz), 8.50(1H, d, J=8.7 Hz), 8.55(1H, t, J=6.0 Hz), 10.07(1H, s).

(2) Preparation of 5-amino-N-[(4-fluorophenyl)methyl]-1-naphthalenesulfonamide hydrochloride.
Yield: 90.4%
$^1$H-NMR(CD$_3$OD, δ): 4.10(2H, s), 6.73-6.80(2H, m), 6.99-7.06(2H, m), 7.71-7.79(3H, m), 8.19(1H, d, J=8.4 Hz), 8.30(1H, dd, J=7.5, 1.2 Hz), 8.81(1H, d, J=7.8 Hz).

Example 12

Preparation of 5-amino-N-[(2,6-difluorophenyl)methyl]-1-naphthalenesulfonamide hydrochloride (Compound No. 12)

(1) Preparation of N-[5-[[[(2,6-difluorophenyl)methyl]amino]sulfonyl]-1-naphthalenyl]acetamide.
Yield: 75.9%
$^1$H-NMR(DMSO-d$_6$, δ): 2.20(3H, s), 4.07(2H, d, J=5.7 Hz), 6.79-6.87(2H, m), 7.21(tt, J=8.4, 6.6 Hz), 7.58-7.65(2H, m), 7.74(1H, d, J=7.2 Hz), 8.11(1H, d, J=7.2 Hz), 8.80(1H, d, J=8.4 Hz), 8.45(1H, d, J=8.7 Hz), 8.65(1H, t, J=5.7 Hz), 10.04(1H, s).

(2) Preparation of 5-amino-N-[(2,6-difluorophenyl)methyl]-1-naphthalenesulfonamide hydrochloride.
Yield: 79.5%
$^1$H-NMR(CD$_3$OD, δ): 4.23(2H, s), 6.50-6.58(2H, m), 7.02(1H, tt, J=8.4, 6.6 Hz), 7.66(3H, m), 8.14(1H, dt, J=8.4, 1.2 Hz), 8.32(1H, dd, J=8.4, 1.2 Hz), 8.75(1H, ddd, J=7.8, 2.1, 1.2 Hz).

Example 13

Preparation of 5-amino-N-[(3,4-difluorophenyl)methyl]-1-naphthalenesulfonamide hydrochloride (Compound No. 13)

(1) Preparation of N-[5-[[[(3,4-difluorophenyl)methyl]amino]sulfonyl]-1-naphthalenyl]acetamide.
Yield: 71%
$^1$H-NMR(DMSO-d$_6$, δ): 2.20(3H, s), 4.04(2H, d, J=6.0 Hz), 6.97(1H, m), 7.18(2H, m), 7.63(1H, dd, J=8.4, 7.8 Hz), 7.68(1H, dd, J=8.4, 8.1 Hz), 7.77(1H, d, J=7.5 Hz), 8.12(1H, d, J=7.5 Hz), 8.33(1H, d, J=8.4 Hz), 8.49(1H, d, J=8.4 Hz), 8.62(1H, t, J=6.0 Hz), 10.06(1H, s).

(2) Preparation of 5 amino-N-[(3,4-difluorophenyl)methyl]-1-naphthalenesulfonamide hydrochloride.
Yield: 59%
$^1$H-NMR(DMSO-d$_6$, δ): 4.02(2H, d, J=6.0 Hz), 6.95(1H, m), 7.18(2H, m), 7.38(1H, d, J=7.2 Hz), 7.60(1H, t, J=7.5 Hz), 7.63(1H, dd, J=8.4, 7.5 Hz), 8.12(1H, d, J=7.2 Hz), 8.29(1H, d, J=8.7 Hz), 8.34(1H, d, J=8.4 Hz), 8.63(1H, t, J=6.0 Hz).

Example 14

Preparation of 5-amino-N-[(3,5-difluorophenyl)methyl]-1-naphthalenesulfonamide hydrochloride (Compound No. 14)

(1) Preparation of N-[5-[[[(3,5-difluorophenyl)methyl]amino]sulfonyl]-1-naphthalenyl]acetamide.
Yield: 75.9%
$^1$H-NMR(DMSO-d$_6$, δ): 2.20(3H, s), 4.08(2H, d, J=6.3 Hz), 6.80-6.86(2H, m), 6.96(1H, tt, J=9.3, 2.4 Hz), 7.63(1H, dd, J=8.4, 7.5 Hz), 7.66-7.72(1H, m), 7.77(1H, d, J=7.5 Hz), 8.18(1H, dd, J=7.2, 1.2 Hz), 8.33(1H, d, J=8.4 Hz), 8.48(1H, d, J=8.4 Hz), 8.68(1H, t, J=6.8 Hz), 10.06(1H, s).

(2) Preparation of 5-amino-N-[(3,5-difluorophenyl)methyl]-1-naphthalenesulfonamide hydrochloride.
Yield: 76.9%
$^1$H-NMR(CD$_3$OD, δ): 4.88(2H, s), 8.59-6.65(3H, m), 7.73-7.82(3H, m), 8.20(1H, dt, J=8.7, 1.2 Hz), 8.33(1H, dd, J=7.5, 1.2 Hz), 8.33(1H, dt, J=8.4, 1.2 Hz).

Example 15

Preparation of 5-amino-N-[(2-methylphenyl)methyl]-1-naphthalenesulfonamide hydrochloride (Compound No. 15)

(1) Preparation of N-[5-[[[(2-methylphenyl)methyl]amino]sulfonyl]-1-naphthalenyl]acetamide.
Yield: 74%
$^1$H-NMR(DMSO-d$_6$, δ): 2.10(3H, s), 2.20(3H, s), 3.99 (2H, s), 7.05(3H, m), 7.16(1H, d, J=7.2 Hz), 7.62(1H, dd, J=8.4, 7.5 Hz), 7.67(1H, t, J=8.4 Hz), 7.76(1H, d, J=7.5H), 8.14(1H, d, J=7.2 Hz), 8.33(1H, d, J=8.4 Hz), 8.37(1H, brs), 8.56(1H, d, J=8.4 Hz), 10.07(1H, s).

(2) Preparation of 5-amino-N-[(2-methylphenyl)methyl]-1-naphthalenesulfonamide hydrochloride.
Yield: 88%
$^1$H-NMR(DMSO-d$_6$, δ): 2.09(3H, s), 3.99(2H, d, J=4.8 Hz), 7.05(3H, m), 7.15(1H, d, J=7.5 Hz), 7.41(1H, d, J=7.8 Hz), 7.60(1H, ddd, J=8.1, 7.8, 1.5 Hz), 7.65(1H, ddd, J=7.5, 7.2, 1.8 Hz), 8.15(1H, dd, J=7.6, 1.2 Hz), 8.36(3H, m).

Example 16

Preparation of 5-amino-N-[(3-methylphenyl)methyl]-1-naphthalenesulfonamide hydrochloride (Compound No. 16)

(1) Preparation of N-[5-[[[(3-methylphenyl)methyl]amino]sulfonyl]-1-naphthalenyl]acetamide.
Yield: 82.4%
$^1$H-NMR(DMSO-d$_6$, δ): 2.10(3H, s), 2.20(3H, s), 4.00 (2H, d, J=6.0 Hz), 6.86(1H, 2), 6.90-6.95(2H, m), 7.05(1H, t, J=7.5 Hz), 7.59-7.70(2H, m), 7.76(1H, d, J=7.2 Hz), 8.12(1H, dd, J=7.5, 1.2 Hz), 8.32(1H, d, J=8.4 Hz), 8.48-8.53(2H, m), 10.06(1H, s).

(2) Preparation of 5-amino-N-[(3-methylphenyl)methyl]-1-naphthalenesulfonamide hydrochloride.
Yield: 85.9%
$^1$H-NMR(DMSO-d$_6$, δ): 2.11(3H, s), 3.99(2H, d, J=6.0 Hz), 6.86(1H, s), 6.92(2H, t, J=8.4 Hz), 7.05(1H, t, J=7.8 Hz), 7.36(1H, d, J=7.2 Hz), 7.56-7.64(2H, in), 8.12(1H, d, J=7.5 Hz), 8.31(1H, d, J=6.9 Hz), 8.33(1H, d, J=7.8 Hz), 8.48(1H, t, J=6.0 Hz).

Example 17

Preparation of 5-amino-N-[(4-methylphenyl)methyl]-1-naphthalenesulfonamide hydrochloride (Compound No. 17)

(1) Preparation of N-[5-[[[(4-methylphenyl)methyl]amino]sulfonyl]-1-naphthalenyl]acetamide.
Yield: 45.0%
$^1$H-NMR(DMSO-d$_6$, δ): 2.20(3H, s), 2.21(3H, s), 3.97 (2H, d, J=6.0 Hz), 6.97-7.05(3H, m), 7.61-7.69(2H, m), 7.58 (1H, d, J=7.5 Hz), 8.13(1H, dd, J=7.5, 1.2 Hz), 8.33(1H, d, J=8.7 Hz), 8.47(1H, t, J=6.0 Hz), 8.52(1H, d, J=8.7 Hz), 10.06(1H, s).

(2) Preparation of 5-amino-N-[(4-methylphenyl)methyl]-1-naphthalene sulfonamide hydrochloride.
Yield: 74.4%
$^1$H-NMR(DMSO-d$_6$, δ): 2.22(3H, s), 3.96(2H, d, J=6.0 Hz), 6.98-7.04(3H, m), 7.30-7.36(1H, m), 7.55-7.65(2H, m), 8.12(1H, dd, J=7.2, 10.9 Hz), 8.28-8.31(1H, m), 8.35(1H, d, J=8.4 Hz), 8.45(1H, t, J=6.0 Hz).

Example 18

Preparation of 5-amino-N-[[4-(1,1-dimethylethyl)phenyl]methyl]-1-naphthalenesulfonamide hydrochloride (Compound No. 18)

(1) Preparation of N-[5-[[[[4-(1,1-dimethylethyl)phenyl]methyl]amino]sulfonyl]-1-naphthalenyl]acetamide.
Yield: 78.1%
$^1$H-NMR(CDCl$_3$, δ): 1.25(9H, s), 2.36(3H, brs), 4.04(2H, d, J=5.7 Hz), 4.82(1H, t, J=6.7 Hz), 7.02(2H, d, J=8.4 Hz), 7.22(2H, d, J=8.7 Hz), 7.51-7.65(3H, m), 7.84(1H, d, J=7.2 Hz), 8.12(1H, d, J=8.4 Hz), 8.28(1H, d, J=7.2 Hz), 8.51(1H, d, J=8.7 Hz).

(2) Preparation of 5-amino-N-[[4-(1,1-dimethylethyl)phenyl]methyl]-1-naphthalenesulfonamide hydrochloride.
Yield: 81.6%
$^1$H-NMR(DMSO-d$_6$, δ): 1.22(9H, s), 3.94(2H, d, J=6.0 Hz), 7.01(1H, d, J=7.5 Hz), 7.07(2H, d, J=8.4 Hz), 7.21(2H, d, J=8.1 Hz), 7.45(1H, t, J=8.1 Hz), 7.50(1H, t, J=8.4 Hz), 8.01(1H, t, J=9.0 Hz), 8.06(1H, d, J=6.6 Hz), 8.31-8.36(2H, m).

Example 19

Preparation of 5-amino-N-[[2-(trifluoromethyl)phenyl]methyl]-1-naphthalenesulfonamide hydrochloride (Compound No. 19)

(1) Preparation of N-[5-[[[[2(trifluoromethyl)phenyl]methyl]amino]sulfonyl]-1-naphthalenyl]acetamide.
Yield: 47%
$^1$H-NMR(DMSO-d$_6$, δ): 2.20(3H, s), 4.21(2H, d, J=6.0 Hz), 7.39(1H, dd, J=7.8, 7.2 Hz), 7.48(1H, dd, J=8.1, 6.9 Hz), 7.62(3H, m), 7.70(1H, dd, J=8.4, 7.5 Hz), 7.80(1H, d, J=7.5 Hz), 8.12(1H, dd, J=7.2, 0.9 Hz), 8.33(1H, d, J=8.4 Hz), 8.54(1H, d, J=8.4 Hz), 8.74(1H, t, J=6.0 Hz), 10.07(1H, s).

(2) Preparation of 5-amino-N-[(2-(trifluoromethyl)phenyl]methyl]-1-naphthalenesulfonamide hydrochloride.
Yield: 67%
$^1$H-NMR(DMSO-d$_6$, δ): 4.20(2H, d, J=6.0 Hz), 7.39(1H, dd, J=7.8, 7.5 Hz), 7.46(1H, dd, J=8.7, 8.1 Hz), 7.49(1H, dd, J=8.7, 6.9 Hz), 7.62(4H, m), 8.13(1H, dd, J=7.5, 0.9 Hz), 8.35(1H, d, J=8.4 Hz), 8.38(1H, d, J=9.0 Hz), 8.77(1H, t, J=6.0 Hz).

Example 20

Preparation of 5-amino-N-[[3-(trifluoromethyl)phenyl]methyl]-1-naphthalenesulfonamide hydrochloride (Compound No. 20)

(1) Preparation of N-[5-[[[[3-(trifluoromethyl)phenyl]methyl]amino]sulfonyl]-1-naphthalenyl]acetamide.
Yield: 71.5%
$^1$H-NMR(DMSO-d$_6$, δ): 2.20(3H, s), 4.15(2H, d, J=6.3 Hz), 7.37-7.49(4H, m), 7.62(1H, dd, J=8.4, 7.5 Hz), 7.65-7.71(1H, m), 7.76(1H, d, J=7.5 Hz), 8.13(1H, dd, J=7.5, 0.9 Hz), 8.32(1H, d, J=8.4 Hz), 8.49(1H, d, J=8.4 Hz), 8.68(1H, t, J=6.3 Hz), 10.06(1H, s).

(2) Preparation of 5-amino-N-[[3-(trifluoromethyl)phenyl]methyl]-1-naphthalenesulfonamide hydrochloride.

Yield: 74.0%

$^1$H-NMR(CD$_3$OD, δ): 4.23(2H, s), 7.21-7.36(4H, m), 7.69-7.80(3H, m), 8.16(1H, dt, J=8.7, 1.2 Hz), 8.32(1H, dd, J=7.5, 1.2 Hz), 8.82(1H), dt, J=8.7, 1.2 Hz).

Example 21

Preparation of 5-amino-N-[[4-(trifluoromethyl)phenyl]methyl]-1-naphthalenesulfonamide hydrochloride (Compound No. 21)

(1) Preparation of N-[5-[[[[4-(trifluoromethyl)phenyl]methyl)amino]sulfonyl]-1-naphthalenyl]acetamide.

Yield: 63.8%

$^1$H-NMR(DMSO-d$_6$, δ): 2.20(3H, s), 4.18(2H, d, J=6.3 Hz), 7.39(2H, d, J=7.8 Hz), 7.56(2H, d, J=8.4 Hz), 7.61-7.72 (2H, m), 7.78(1H, d, J=7.2 Hz), 8.13(1H, dd, J=7.5, 1.2 Hz), 8.34(1H, d, J=8.7 Hz), 8.50(1H, d, J=8.1 Hz), 8.68(1H, t, J=6.3 Hz), 10.07(1H, s).

(2) Preparation of 5-amino-N-[[4-(trifluoromethyl)phenyl]methyl]-1-naphthalenesulfonamide hydrochloride.

Yield: 79.8%

$^1$H-NMR(CD$_3$OD, δ): 4.20(2H, s), 7.24(2H, d, J=8.1 Hz), 7.39(2H, d, J=8.4 Hz), 7.70-7.80(3H, m), 8.21(1H, dt, J=9.0, 1.2 Hz), 8.82(1H, dd, J=7.2, 1.2 Hz), 8.82(1H, dt, J=8.4, 1.2 Hz).

Example 22

Preparation of 5-amino-N-[[[1,1'-biphenyl]-4-yl]methyl]-1-naphthalenesulfonamide hydrochloride (Compound No. 22)

(1) Preparation of N-[5-[[[[[1,1'-biphenyl]-4-yl]methyl]amino]sulfonyl]-1-naphthalenyl]acetamide.

Yield: 75.3%

$^1$H-NMR(DMSO-d$_6$, δ): 2.20(3H, s), 4.08(2H, d, J=6.3 Hz), 7.24(2H, d, J=8.1 Hz), 7.32-7.87(1H, m), 7.41-7.49(4H, m), 7.57-7.66(3H, m), 7.70(1H, d, J=8.7 Hz), 7.79(1H, d, J=7.5 Hz), 8.15(1H, dd, J=7.5, 1.2 Hz), 8.33(1H, d, J=8.4 Hz), 8.53-8.59(2H, m), 10.04(1H, s).

(2) Preparation of 5-amino-N-[[[1,1'-biphenyl]-4-yl]methyl]-1-naphthalenesulfonamide hydrochloride.

Yield: 82.5%

$^1$H-NMR(DMSO-d$_6$, δ): 4.07(2H, d, J=6.0 Hz), 7.25(2H, d, J=8.1 Hz), 7.32-7.52(6H, m), 7.59-7.68(4H, m), 8.17(1H, d, J=7.2 Hz), 8.36(2H, d, J=8.4 Hz), 8.57(1H, d, J=6.0 Hz).

Example 23

Preparation of 5-amino-N-[[[4'-methyl-1,1'-biphenyl]-2-yl]methyl]-1-naphthalenesulfonamide hydrochloride (Compound No. 23)

(1) Preparation of N-[5-[[[[4'-methyl-1,1'-biphenyl]-2-yl]methyl]amino]sulfonyl]-1-naphthalenyl]acetamide.

Yield: 67%

$^1$H-NMR(DMSO-d$_6$, δ): 2.20(3H, s), 2.26(3H, s), 3.90 (2H, d, J=5.1 Hz), 7.01(4H, m), 7.09(1H, m), 7.22(2H, m), 7.37(1H, m), 7.56(1H, dd, J=8.4, 7.5 Hz), 7.67(1H, dd, J=8.7, 7.5 Hz), 7.78(1H, d, J=7.5 Hz), 7.97(1H, d, J=7.2 Hz), 8.31 (1H, d, J=8.4 Hz), 8.43(1H, t, J=5.1 Hz), 8.51(1H, d, J=8.4 Hz), 10.06(1H, s).

(2) Preparation of 5-amino-N-[[[4'-methyl-1,1'-biphenyl]-2-yl]methyl]-1-naphthalenesulfonamide hydrochloride.

Yield: 75%

$^1$H-NMR(DMSO-d$_6$, δ): 2.29(3H, s), 3.91(2H, d, J=5.7 Hz), 7.06(5H, m), 7.18-7.27(2H, m), 7.37(2H, m), 7.55(1H, dd, J=8.1, 7.5 Hz), 7.57(1H, dd, J=8.1, 7.5 Hz), 7.97(1H, dd, J=7.2, 0.9 Hz), 8.80(1H, d, J=9.9 Hz), 8.33(1H, d, J=8.4 Hz), 8.42(1H, t, J=5.7 Hz).

Example 24

Preparation of 5-amino-N-[(2-methoxyphenyl)methyl]-1-naphthalenesulfonamide hydrochloride (Compound No. 24)

(1) Preparation of N-[5-[[[(2-methoxyphenyl)methyl]amino]sulfonyl]-1-naphthalenyl]acetamide.

Yield: 42.8%

$^1$H-NMR(DMSO-d$_6$, δ): 2.20(3H, s), 3.50(3H s), 4.00(2H, d, J=6.0 Hz), 6.74-6.79(2H, m), 7.10-7.18(2H, m), 7.58-7.68 (2H, m), 7.75(2H, d, J=7.5 Hz), 8.10(1H, dd, J=7.5, 0.9 Hz), 8.26-8.32(2H, m), 8.52(1H, d, J=8.7 Hz), 10.05(1H, s).

(2) Preparation of 5-amino-N-[(2-methoxyphenyl)methyl]-1-naphthalenesulfonamide hydrochloride.

Yield: 60.0%

$^1$H-NMR(DMSO-d$_6$, δ): 3.52(3H s), 3.98(2H, d, J=6.3 Hz), 6.74-6.79(2H, m), 7.11-7.18(2H, m), 7.27-7.30(1H, m), 7.52-7.61(2H, m), 8.08(1H, d, J=6.9 Hz), 8.21-8.27(2H, m), 8.32(1H, d, J=8.7 Hz).

Example 25

Preparation of 5-amino-N-[(3-methoxyphenyl)methyl]-1-naphthalenesulfonamide hydrochloride (Compound No. 25)

(1) Preparation of N-[5-[[[(3-methoxyphenyl)methyl]amino]sulfonyl]-1-naphthalenyl]acetamide.

Yield: 75.9%

$^1$H-NMR(DMSO-d$_6$, δ): 2.20(3H, s), 3.34(3H, s), 4.03 (2H, d, J=6.0 Hz), 6.64-6.73(3H, m), 7.09(1H, t, J=7.8 Hz), 7.60-7.77(3H, m), 8.13(1H, dd, J=7.5, 1.2 Hz), 8.33(1H, d, J=8.7 Hz), 8.52-8.57(2H, m), 10.07(1H, s).

(2) Preparation of 5-amino-N-[(3-methoxyphenyl)methyl]-1-naphthalenesulfonamide hydrochloride.

Yield: 81.6%

$^1$H-NMR(CD$_3$OD, δ): 3.55(3H, s), 4.10(2H, s), 6.55-6.61 (3H, m), 6.94(1H, t, J=8.1 Hz), 7.64-7.79(3H, m), 8.17(1H, dt, J=8.4, 1.2 Hz), 8.31(1H, dd, J=7.5, 1.2 Hz), 8.84(1H, dt, J=8.4, 1.2 Hz).

Example 26

Preparation of 5-amino-N-[(4-methoxyphenyl)methyl]-1-naphthalenesulfonamide hydrochloride (Compound No. 26)

(1) Preparation of N-[5-[[[(4-methoxyphenyl)methyl]amino]sulfonyl]-1-naphthalenyl]acetamide.

Yield: 49.6%

$^1$H-NMR(DMSO-d$_6$, δ): 2.20(3H, s), 3.68(3H, s), 3.95 (2H, d, J=6.0 Hz), 6.72-6.76(2H, d, J=8.4 Hz), 7.05(2H, d, J=8.4 Hz), 7.64(1H, t, J=8.7 Hz), 7.66(1H, t, J=9.0 Hz), 7.76(1H, d, J=7.5 Hz), 8.13(1H, dd, J=7.5, 1.2 Hz), 8.33(1H, d, J=8.7 Hz), 8.44(1H, t, J=6.0 Hz), 8.51(1H, d, J=8.1 Hz), 10.06(1H, s).

(2) Preparation of 5-amino-N-[(4-methoxyphenyl)methyl]-1-naphthalenesulfonamide hydrochloride.
Yield: 76.6%
$^1$H-NMR(DMSO-d$_6$, δ): 3.69(3H, s), 3.93(2H, d, J=6.0 Hz), 6.75(2H, d, J=8.7 Hz), 7.06(2H, d, J=8.4 Hz), 7.19(1H, d, J=7.2 Hz), 7.52(1H, t, J=8.4 Hz), 7.57(1H, t, J=8.4 Hz), 8.10(1H, d, J=7.5 Hz), 8.17(1H, d, J=8.7 Hz), 8.34(1H, d, J=8.4 Hz), 8.36(1H, t, J=5.7 Hz).

Example 27

Preparation of 5-amino-N-[(3,4-methylenedioxyphenyl)methyl]-1-naphthalenesulfonamide hydrochloride (Compound No. 27)

(1) Preparation of N-[5-[[[(3,4-methylenedioxyphenyl)methyl]amino]sulfonyl]-1-naphthalenyl]acetamide.
Yield: 81.4%
$^1$H-NMR(DMSO-d$_6$, δ): 2.20(3H, s), 3.94(2H, s), 5.91 (2H, s), 6.58(1H, dd, J=7.8, 1.2 Hz), 6.66(1H, s), 6.68(1H, d, J=8.1 Hz), 7.63(1H, t, J=7.8 Hz), 7.67(1H, t, J=7.8 Hz), 7.76(1H, d, J=7.5 Hz), 8.12(1H, d, J=6.9 Hz), 8.33(1H, d, J=8.4 Hz), 8.49(1H, d, J=8.4 Hz), 10.08(1H, s).

(2) Preparation of 5-amino-N-[(3,4-methylenedioxyphenyl)methyl]-1-naphthalenesulfonamide hydrochloride.
Yield: 67.1%
$^1$H-NMR(DMSO-d$_6$, δ): 3.93(2H, d, J=6.3 Hz), 5.92(2H, s), 6.57(1H, dd, J=8.1, 1.5 Hz), 6.64(1H, d, J=1.2 Hz), 6.68 (1H, d, J=7.5 Hz), 7.34(1H, d, J=7.5 Hz), 7.55-7.64(2H, m), 8.10(1H, dd, J=7.5, 0.9 Hz), 8.27(1H, d, J=8.4 Hz), 8.33(1H, d, J=8.4 Hz), 8.44(1 Hz, t, J=6.3 Hz).

Example 28

Preparation of 5-amino-N-[(2,3-dimethoxyphenyl)methyl]-1-naphthalenesulfonamide hydrochloride (Compound No. 28)

(1) Preparation of N-[5-[[[(2,3-dimethoxyphenyl)methyl]amino]sulfonyl]-1-naphthalenyl]acetamide.
Yield: 75.8%
$^1$H-NMR(DMSO-d$_6$, δ): 2.20(3H, s), 3.56(3H, s), 3.74 (3H, s), 4.02(2H, s), 6.79-6.84(1H, m), 6.87-6.94(2H, m), 7.63-7.70(2H, m), 7.76(1H, d, J=7.2 Hz), 8.16(1H, dd, J=7.5, 1.2 Hz), 8.34(1H, d, J=8.7 Hz), 8.38(1H, s), 8.54(1H, d, J=8.4 Hz), 10.08(1H, s).

(2) Preparation of 5-amino-N-[(2,3-dimethoxyphenyl)methyl]-1-naphthalenesulfonamide hydrochloride.
Yield: 70.9%
$^1$H-NMR(DMSO-d$_6$, δ): 3.56(3H, s), 3.74(3H, s), 4.08 (2H, d, J=6.0 Hz), 6.79-6.90(3H, m), 7.28(1H, d, J=7.8 Hz), 7.56(1H, t, J=8.4 Hz), 7.62(1H, t, J=8.4 Hz), 8.13(1H, d, J=7.2 Hz), 8.26(1H, d, J=8.1 Hz), 8.33-8.36(2H, m).

Example 29

Preparation of 5-amino-N-[(2,4-dimethoxyphenyl)methyl]-1-naphthalenesulfonamide hydrochloride (Compound No. 29)

(1) Preparation of N-[5-[[[(2,4-dimethoxyphenyl)methyl]amino]sulfonyl]-1-naphthalenyl]acetamide.
Yield: 79%
$^1$H-NMR(DMSO-d$_6$, δ): 2.20(3H, s), 8.42(3H, s), 3.68 (3H, s), 8.91(2H, d, J=5.7 Hz), 6.28(1H, d, J=2.4 Hz), 6.32 (1H, dd, J=8.1, 2.4 Hz), 7.03(1H, d, J=8.1 Hz), 7.60(1H, dd, J=8.4, 7.5 Hz), 7.64(1H, dd, J=8.1, 7.8 Hz), 7.75(1H, d, J=7.5 Hz), 8.06(1H, d, J=7.5 Hz), 8.15(1H, t, J=5.7 Hz), 8.30(1H, d, J=8.4 Hz), 8.50(1H, d, J=8.4 Hz), 10.04(1H, s).

(2) Preparation of 5-amino-N-[(2,4-dimethoxyphenyl)methyl]-1-naphthalenesulfonamide hydrochloride.
Yield: 66%
$^1$H-NMR(DMSO-d$_6$(80° C.), δ): 3.51(3H, s), 3.59(3H, s), 3.73(2H, s), 6.06(1H, m), 6.51(2H, m), 7.07(1H, d, J=7.8 Hz), 7.43(1H, dd, J=8.7, 7.5 Hz), 7.50(1H, brs), 7.52(1H, dd, J=8.4, 7.5 Hz), 8.07(1H, d, J=8.7 Hz), 8.12(1H, d, J=7.5 Hz), 8.32(1H, d, J=8.4 Hz).

Example 30

Preparation of 5-amino-N-[(3,4-dimethoxyphenyl)methyl]-1-naphthalenesulfonamide hydrochloride (Compound No. 30)

(1) Preparation of N-[5-[[[(3,4-dimethoxyphenyl)methyl]amino]sulfonyl]-1-naphthalenyl]acetamide.
Yield: 78.7%
$^1$H-NMR(DMSO-d$_6$, δ): 2.20(3H, s), 3.39(3H, s), 3.65 (3H, s), 3.98(2H, s), 6.53(1H, d, J=2.1 Hz), 6.65(1H, dd, J=8.1, 2.1 Hz), 6.73(1H, d, J=8.1 Hz), 7.59-7.70(2H, m), 7.76(1H, d, J=7.2 Hz), 8.12(1H, dd, J=7.2, 1.2 Hz), 8.32(1H, d, J=8.4 Hz), 8.43(1H, brs), 8.54(1H, d, J=8.4 Hz), 10.06(1H, s).

(2) Preparation of 5-amino-N-[(3,4-dimethoxyphenyl)methyl]-1-naphthalenesulfonamide hydrochloride.
Yield: 54.0%
$^1$H-NMR(DMSO-d$_6$, δ): 3.43(3H, s), 3.66(3H, s ), 3.98 (2H, d, J=6.0 Hz), 6.57(1H, d, J=2.1 Hz), 6.64(1H, dd, J=8.4, 2.1 Hz), 6.73(1H, d, J=7.8 Hz), 7.40(1H, d, J=7.5 Hz), 7.57-7.65(2H, m), 8.13(1H, d, J=7.2 Hz), 8.34(1H, d, J=8.7 Hz), 8.36(1H, d, J=8.4 Hz), 8.46(1H, t, J=6.0 Hz).

Example 31

Preparation of 5-amino-N-[(3,5-dimethoxyphenyl)methyl]-1-naphthalenesulfonamide hydrochloride (Compound No. 31)

(1) Preparation of N-[5-[[[(3,5-dimethoxyphenyl)methyl]amino]sulfonyl]-1-naphthalenyl]acetamide.
Yield: 73.3%
$^1$H-NMR(DMSO-d$_6$, δ): 2.20(3H, s), 3.50(6H, s), 4.00-4.01(2H, m), 6.23(1H, s), 6.23(2H, s), 7.60-7.77(3H, m), 8.13(1H, d, J=7.2 Hz), 8.32(1H, d, J=8.4 Hz), 8.54(2H, d, J=8.1 Hz), 10.07(1H, s).

(2) Preparation of 5-amino-N-[(3,5-dimethoxyphenyl)methyl]-1-naphthalenesulfonamide hydrochloride.
Yield: 73.3%

¹H-NMR(CD₃OD, δ): 3.53(6H, s), 4.09(2H, s), 6.11-6.16 (3H, m), 7.01-7.80(3H, m), 8.17(1H, dt, J=8.4, 1.2 Hz), 8.31 (1H, dd, J=8.4, 1.2 Hz), 8.55(1H, dt, J=8.4, 1.2 Hz).

Example 82

Preparation of 5-amino-N-[(2,4,6-trimethoxyphenyl) methyl]-1-naphthalenesulfonamide hydrochloride (Compound No. 32)

(1) Preparation of N-[5-[[[(2,4,6-trimethoxyphenyl)methyl] amino]sulfonyl]-1-naphthalenyl]acetamide.

Yield: 56.1%

¹H-NMR(DMSO-d₆, δ): 2.20(3H, s), 3.43(6H, s), 3.66 (3H, s), 3.92(2H, d, J=5.1 Hz), 5.91(2H, s), 7.53-7.64(3H, m), 7.73(1H, d, J=7.5 Hz), 8.09(1H, dd, J=7.5, 1.2 Hz), 8.29(1H, d, J=8.4 Hz), 8.45(1H, d, J=8.7 Hz), 10.01(1H, s).

(2) Preparation of 5-amino-N-[(2,4,6-trimethoxyphenyl)methyl]-1-naphthalenesulfonamide hydrochloride.

Yield: 73.3%

¹H-NMR(DMSO-d₆, δ): 8.79(6H, s), 3.85(3H, s), 3.85 (2H, s), 6.30(2H s), 7.05(1H, d, J=9.0 Hz), 7.45(2H, brs), 7.50(1H, dd, J=8.1, 7.5 Hz), 7.84(1H, d, J=9.0 Hz), 8.01(1H, d, J=6.9 Hz), 8.39(1H, d, J=8.4 Hz).

Example 33

Preparation of 5-amino-N-[(3,4,5-trimethoxyphenyl) methyl)-1-naphthalenesulfonamide hydrochloride (Compound No. 33)

(1) Preparation of N-[5-[[[(3,4,5-trimethoxyphenyl)methyl] amino]sulfonyl]-1-naphthalenyl]acetamide.

Yield: 68.6%

¹H-NMR(DMSO-d₆, δ): 2.19(3H, s), 3.44(6H, s), 3.50 (3H, s), 4.03(2H, d, J=6.0 Hz), 6.27(2H, s), 7.60(1H, dd, J=8.1, 7.5 Hz), 7.68(1H, t, J=8.1 Hz), 7.76(1H, d, J=7.2 Hz), 8.12(1H, dd, J=7.2, 1.2 Hz), 8.31(1H, d, J=8.7 Hz), 8.51-8.55 (2H, m), 10.04(1H, s).

(2) Preparation of 5-amino-N-[(3,4,5-trimethoxyphenyl)methyl]-1-naphthalenesulfonamide hydrochloride.

Yield: 62.3%

¹H-NMR(DMSO-d₆, δ): 3.45(6H, s), 3.52(8H, s), 4.02 (2H, d, J=6.0 Hz), 6.31(2H, s), 7.36(1H, d, J=6.9 Hz), 7.56-7.68(2H, m), 8.12(1H, dd, J=7.5, 0.9 Hz), 8.32(1H, d, J=8.4 Hz), 8.34(1H, d, J=8.4 Hz), 8.51(1H, t, J=6.0 Hz).

Example 34

Preparation of 5-amino-N-[(2-ethoxyphenyl)methyl]-1-naphthalenesulfonamide (Compound No. 34)

(1) Preparation of N-[5-[[[(2-ethoxyphenyl)methyl]amino] sulfonyl]-1-naphthalenyl]acetamide.

Yield: 75%

¹H-NMR(DMSO-d₆, δ): 1.16(3H, t, J=6.9 Hz), 2.20(3H, s), 3.82(2H, q, J=6.9 Hz), 4.02(2H, d, J=5.7 Hz), 6.76(2H, m), 7.12(1H, dd, J=8.1, 7.8 Hz), 7.18(1H, d, J=7.2 Hz), 7.61(1H, dd, J=8.4, 7.2 Hz), 7.65(1H, dd, J=8.1, 7.8 Hz), 7.75(1H, d, J=7.5 Hz), 8.09(1H, d, J=7.5 Hz), 8.27(1H, t, J=5.7 Hz), 8.54(1H, d, J=8.4 Hz), 10.05(1H, s).

(2) Preparation of 5-amino-N-[(2-ethoxyphenyl)methyl]-1-naphthalenesulfonamide.

Preparation was carried out by in the same manner as the method of Example 1(2). However the compound was isolated as a free form without being converted to hydrochloride.

Yield: 68%

¹H-NMR(DMSO-d₆, δ): 1.19 (3H, t, J=6.9 Hz), 3.86(2H, q, J=6.9 Hz), 3.97(2H, d, J=6.0 Hz), 5.95(2H, s), 6.77(1H, m), 6.78(1H, d, J=7.5 Hz), 6.81(1H, d, J=6.6 Hz), 7.13(1H, ddd, J=8.1, 7.5, 1.8 Hz), 7.21(1H, dd, J=7.5, 1.5 Hz), 7.36(1H, dd, J=8.4, 8.1 Hz), 7.41(1H, dd, J=8.4, 7.5 Hz), 7.84(1H, d, J=8.4 Hz), 8.00(1H, d, J=6.9 Hz), 8.05(1H, t, J=6.0 Hz), 8.34(1H, d, J=8.4 Hz).

Example 35

Preparation of 5-amino-N-[[3-(phenylmethoxy)phenyl]methyl]-1-naphthalenesulfonamide hydrochloride (Compound No. 35)

(1) Preparation of N-[5-[[[[3-(phenylmethoxy)phenyl]methyl]amino]sulfonyl]-1-naphthalenyl]acetamide.

Yield: 73.0%

¹H-NMR(DMSO-d₆, δ): 2.19(3H, s), 4.02(2H, d, J=6.3 Hz), 4.87(2H, s), 6.72-6.79(3H, m), 7.09(1H, dd, J=8.7, 7.5 Hz), 7.31-7.39(5H, m), 7.60-7.71(2H, m), 7.77(1H, d, J=7.2 Hz), 8.13(1H, dd, J=7.5, 0.9 Hz), 8.52-8.56(2H, m), 10.05 (1H, s).

(2) Preparation of 5-amino-N-[[3-(phenylmethoxy)phenyl] methyl]-1-naphthalenesulfonamide hydrochloride.

Preparation was carried out in the same manner as the method of Example 1(2), except that the reaction time was 20 minutes.

Yield: 68.9%

¹H-NMR(DMSO-d₆, δ): 4.00(2H, d, J=6.3 Hz), 4.86(2H, s), 6.73(1H, d, J=7.2 Hz), 6.76-6.78(2H, m), 7.09(2H, dd, J=8.7, 7.5 Hz), 7.31-7.40(5H, m), 7.51(2H, q, J=8.4 Hz), 8.08(1H, d, J=7.2 Hz), 8.12(1H, d, J=8.7 Hz), 8.34(1H, d, J=8.7 Hz), 8.44(1H, t, J=6.3 Hz).

Example 36

Preparation of 5-amino-N-[[4-(phenylmethoxy)phenyl]methyl]-1-naphthalenesulfonamide hydrochloride (Compound No. 36)

(1) Preparation of N-[5-[[[[4-(phenylmethoxy)phenyl]methyl]amino]sulfonyl]-1-naphthalenyl]acetamide.

Yield: 72.5%

¹H-NMR(DMSO-d₆, δ): 2.19(3H, s), 3.95(2H, d, J=6.0 Hz), 5.03(2H, s), 6.82(2H, d, J=8.7 Hz), 7.05(2H, d, J=8.7 Hz), 7.31-7.43(5H, m), 7.60-7.69(2H, m), 7.76(1H, d, J=7.5 Hz), 8.12(1H, dd, J=7.5, 1.2 Hz), 8.33(1H, d, J=8.7 Hz), 8.43(1H, t, J=6.0 Hz), 8.51(1H, d, J=8.7 Hz), 10.05(1H, s).

(2) Preparation of 5-amino-N-[[4-(phenylmethoxy)phenyl] methyl]-1-naphthalenesulfonamide hydrochloride.

Yield: 66.7%

¹H-NMR(DMSO-d₆, δ): 3.93(2H, d, J=6.0 Hz), 5.04(2H, s), 6.83(2H, dt, J=9.0, 2.7 Hz), 7.06(2H, dt, J=8.7, 2.4 Hz), 7.23(1H, d, J=7.8 Hz), 7.29-7.44(5H, m), 7.53(1H, dd, J=8.7, 7.8 Hz), 7.58(1H, dd, J=8.4, 7.2 Hz), 8.10(1H, dd, J=7.5, 1.2 Hz), 8.20(1H, d, J=9.0 Hz), 8.33-8.39(2H, m).

Example 37

Preparation of 5-amino-N-[(6-methoxy-2-naphthalenyl)methyl]-1-naphthalenesulfonamide hydrochloride (Compound No. 37)

(1) Preparation of N-[5-[[[(6-methoxy-2-naphthalenyl)methyl]amino]sulfonyl]-1-naphthalenyl]acetamide.

Yield: 87%

$^1$H-NMR(DMSO-$d_6$, δ): 2.20(3H, s), 3.85(3H, s), 4.15 (2H, d, J=6.0 Hz), 7.10(1H, dd, J=8.7, 2.4 Hz), 7.24(1H, dd, J=8.7, 1.2 Hz), 7.52(1H, s), 7.63(3H, m), 7.70(1H, dd, J=8.1, 7.8 Hz), 7.78(1H, d, J=7.5 Hz), 8.17(1H, d, J=7.2 Hz), 8.31 (1H, d, J=8.4 Hz), 8.57(1H, d, J=8.7 Hz), 8.60(1H, t, J=6.0 Hz), 10.06(1H, s).

(2) Preparation of 5-amino-N-[(6-methoxy-2-naphthalenyl)methyl]-1-naphthalenesulfonamide hydrochloride.

Yield: 83%

$^1$H-NMR(DMSO-$d_6$, δ): 3.85(3H, s), 4.14(2H, d, J=6.0 Hz), 7.11(1H, d, J=8.7, 2.4 Hz), 7.24(2H, m), 7.31(1H, d, J=7.8 Hz), 7.59(3H, m), 7.65(1H, d, J=8.7 Hz), 8.16(1H, dd, J=7.2, 0.9 Hz), 8.31(1H, d, J=7.8 Hz), 8.34(1H, d, J=8.4 Hz), 8.57(1H, t, J=6.0 Hz).

Example 38

Preparation of 5-amino-N-[(3-hydroxyphenyl)methyl]-1-naphthalenesulfonamide hydrochloride (Compound No. 38)

Preparation was carried out in the same manner as the method of Example 1(2) using N-[5-[[[[3-(phenylmethoxy)phenyl]methyl]amino]sulfonyl]-1-naphthalenyl]acetamide (compound of Example 35(1)), provided that the reaction time was 8.5 hours.

Yield: 83.6%

$^1$H-NMR(DMSO-$d_6$, δ): 3.91(2H, d, J=6.0 Hz), 6.56-6.61 (2H, m), 6.67-6.69(1H, m), 7.00(1H, t, J=7.8 Hz), 7.28(1H, d, J=7.8 Hz), 7.56(1H, t, J=7.8 Hz), 7.62(1H, t, J=7.8 Hz), 8.12(1H, d, J=7.5 Hz), 8.25(1H, d, J=8.7 Hz), 8.35(1H, d, J=8.4 Hz), 8.43(1H, t, J=6.0 Hz).

Example 39

Preparation of 5-amino-N-[(3,4-dihydroxyphenyl)methyl]-1-naphthalenesulfonamide hydrochloride (Compound No. 39)

(1) Preparation of N-[5-[[[(3,4-dihydroxyphenyl)methyl]amino]sulfonyl]-1-naphthalenyl]acetamide.

Yield: 43.5%

$^1$H-NMR(DMSO-$d_6$, δ): 2.20(3H, s), 3.83(2H, d, J=6.0 Hz), 6.41(1H, dd, J=7.8, 1.8 Hz), 6.57(1H, d, J=7.8 Hz), 6.66(1H, d, J=1.8 Hz), 7.63-7.70(2H, m), 7.76(1H, d, J=7.5 Hz), 8.14(1H, dd, J=7.5, 1.2 Hz), 8.33-8.38(2H, m), 8.53(1H, d, J=8.7 Hz), 8.74(1H, s), 8.82(1H, s), 10.07(1H, s).

(2) Preparation of 5-amino-N-[(3,4-dihydroxyphenyl)methyl]-1-naphthalenesulfonamide hydrochloride.

Yield: 28.3%

$^1$H-NMR(CD$_3$OD, δ): 3.95(2H, s), 6.30(1H, dd, J=8.1, 2.1 Hz), 6.40-6.43(2H, m), 7.66-7.76(3H, m), 8.18(1H, dt, J=8.4, 1.2 Hz), 8.27(1H, dd, J=7.5, 1.2 Hz), 8.79(1H, dd, J=8.4, 0.9 Hz).

Example 40

Preparation of 5-amino-N-[(4-hydroxy-8-methoxyphenyl)methyl]-1-naphthalenesulfonamide hydrochloride (Compound No. 40)

(1) Preparation of N-5-[[[(4-hydroxy-3-methoxyphenyl)methyl]amino]sulfonyl]-1-naphthalenesulfonamide.

Yield: 66.3%

$^1$H-NMR(DMSO-$d_6$, δ): 2.20(3H, s), 3.94(2H, d, J=6.0 Hz), 6.51-6.59(3H, m), 7.60-7.71(2H, m), 7.66(1H, d, J=7.2 Hz), 8.13(1H, d, J=7.5 Hz), 8.33(1H, d, J=8.4 Hz), 8.41(1H, t, J=6.0 Hz), 8.55(1H, d, J=8.4 Hz), 8.77(1H, brs), 10.06(1H, s).

(2) Preparation of 5-amino-N-[(4-hydroxy-3-methoxyphenyl)methyl]-1-naphthalenesulfonamide hydrochloride.

Yield: 27.6%

$^1$H-NMR(DMSO-$d_6$, δ): 3.46(3H, s), 3.92(2H, d, J=6.0 Hz), 6.51-6.59(3H, m), 7.18(1H, d, J=6.9 Hz), 7.49-7.61(2H, m), 8.10(1H, dd, J=7.2, 0.9 Hz), 8.19(1H, d, J=7.8 Hz), 8.31-8.35(2H, m).

Example 41

Preparation of 5-amino-N-[(3 nitrophenyl)methyl]-1-naphthalenesulfonamide hydrochloride (Compound No. 41)

(1) Preparation of N-[5-[[[(3-nitrophenyl)methyl]amino]sulfonyl]-1-naphthalenyl]acetamide.

Yield: 75.1%

$^1$H-NMR(DMSO-$d_6$, δ): 2.18(3H, s), 4.18(2H, d, J=6.0 Hz), 7.37(1H, t, J=7.8 Hz), 7.51(1H, d, J=7.8 Hz), 7.58(1H, dd, J=8.7, 7.5 Hz), 7.65(1H, t, J=7.5 Hz), 7.68-7.71(1H, m), 7.91-7.97(2H, m), 8.11(1H, dd, J=7.5, 0.9 Hz), 8.25(1H, d, J=8.4 Hz), 8.44 (1H, d, J=8.1 Hz), 8.75(1H, t, J=6.3 Hz), 10.05(1H, s).

(2) Preparation of 5-amino-N-[(3-nitrophenyl)methyl]-1-naphthalenesulfonamide hydrochloride.

Yield: 76.4%

$^1$H-NMR(CD$_3$OD, δ): 4.29(2H, s), 7.27(1H, t, J=8.1 Hz), 7.39-7.42(1H, m), 7.66-7.79(4H, m), 7.87(1H, ddd, J=8.1, 2.4, 1.2 Hz), 8.12(1H, dt, J=8.7, 0.9 Hz), 8.30(1H, dd, J=7.5, 1.2 Hz), 8.79(1H, dt, J=8.4, 1.2 Hz).

Example 42

Preparation of 5-amino-N-[(4-nitrophenyl)methyl]-1-naphthalenesulfonamide hydrochloride (Compound No. 42)

(1) Preparation of N-[5-[[[(4-nitrophenyl)methyl]amino]sulfonyl]-1-naphthalenyl]acetamide.

Yield: 73.6%

$^1$H-NMR(DMSO-$d_6$, δ): 2.20(3H, s), 4.18(2H, d, J=5.7 Hz), 7.44(2H, d, J=9.0 Hz), 7.61-7.78(3H, m), 8.05(2H, d, J=8.7 Hz), 8.14(1H, dd, J=7.5, 0.9 Hz), 8.33(1H, d, J=8.4 Hz), 8.50(1H, d, J=8.4 Hz), 8.75(1H, t, J=6.3 Hz), 10.05(1H, s).

(2) Preparation of 5-amino-N-[(4-nitrophenyl)methyl)]-1-naphthalenesulfonamide hydrochloride.

Yield: 84.7%

$^1$H-NMR(DMSO-$d_6$, δ): 4.16(2H, d, J=6.3 Hz), 7.30(1H, d, J=7.5 Hz), 7.41-7.45(2H, m), 7.55-7.63(2H, m), 8.01-8.06

(2H, m), 8.12(1H, dd, J=7.5, 1.2 Hz), 8.28(1H, d, J=8.1 Hz), 8.34(1H, d, J=8.7 Hz), 8.72(1H, t, J=6.3 Hz).

Example 43

Preparation of 5-amino-N-[(2-aminophenyl)methyl]-1-naphthalenesulfonamide dihydrochloride (Compound No. 43)

(1) Preparation of N-[5-[[[(2-aminophenyl)methyl]amino]sulfonyl-1-naphthalenyl]acetamide.
Yield: 72.0%
$^1$H-NMR(DMSO-$d_6$, δ): 2.2.0(3H, s), 3.84(2H, s), 4.89(2H, s), 6.44(1H, td, J=7.5, 1.2 Hz), 6.57-6.60(1H, m), 6.91-6.97(2H, m), 7.64-7.71(2H, m), 7.77(1H, d, J=7.2 Hz), 8.18(1H, dd, J=7.5, 1.2 Hz), 8.35(1H, d, J=8.4 Hz), 8.55(1H, d, J=8.4 Hz), 10.08(1H, s).

(2) Preparation of 5-amino-N-[(2-aminophenyl)methyl]-1-naphthalenesulfonamide dihydrochloride.
Yield: 82.6%
$^1$H-NMR(CD$_3$OD, δ): 4.24(2H, s), 7.27-7.31(2H, m), 7.34-7.43(2H, m), 7.71(1H, dd, J=7.8, 1.2 Hz), 7.77-7.84(2H, m), 8.29(1H, d, J=8.4 Hz), 8.38(1H, dd, J=7.5, 1.2 Hz), 8.81(1H, d, J=8.7 Hz).

Example 44

Preparation of 5-amino-N-[(3-aminophenyl)methyl]-1-naphthalenesulfonamide dihydrochloride (Compound No. 44)

(1) Preparation of N-[5-[[[(3-aminophenyl)methyl]amino]sulfonyl]-1-naphthalenyl]acetamide.
Yield: 48.8%
$^1$H-NMR(DMSO-$d_6$, δ): 2.20(3H, s), 3.85(2H, s), 4.97(2H, s), 6.30(1H, d, J=7.8 Hz), 6.38-6.44(2H, m), 6.85(1H, t, J=7.8 Hz), 7.63-7.70(2H, m), 7.75(1H, d, J=7.2 Hz), 8.15(1H, dd, J=7.2, 0.9 Hz), 8.34(1H, d, J=8.7 Hz), 8.38-8.42(1H, m), 8.55(1H, d, J=8.4 Hz), 10.07(1H, s).

(2) Preparation of 5-amino-N-[(3-aminophenyl)methyl]-1-naphthalenesulfonamide dihydrochloride.
Yield: 86.1%
$^1$H-NMR(CD$_3$OD, δ): 4.15(2H, s), 7.20-7.26(2H, m), 7.31-7.39(2H, m), 7.71(1H, d, J=7.5 Hz), 7.77-7.83(2H, m), 8.26(1H, dt, J=8.7, 0.9 Hz), 8.35(1H, dd, J=7.5, 1.2 Hz), 8.81(1H, d, J=8.4 Hz).

Example 45

Preparation of 5-amino-N-[(4-aminophenyl)methyl]-1-naphthalenesulfonamide dihydrochloride. (Compound No. 45)

(1) Preparation of N-[5-[[[(4-aminophenyl)methyl]amino]sulfonyl]-1-naphthalenyl]acetamide.
Yield: 67.4%
$^1$H-NMR(DMSO-$d_6$, δ): 2.20(3H, s), 3.82(2H, d, J=6.0 Hz), 4.98(2H, s), 6.39(2H, d, J=8.4 Hz), 8.79(2H, d, J=8.4 Hz), 7.62-7.69(2H, m), 7.76(1H, d, J=7.2 Hz), 8.14(1H, dd, J=7.2, 0.9 Hz), 8.29(1H, t, J=6.0 Hz), 8.34(1H, d, J=8.4 Hz), 8.53(1H, d, J=8.4 Hz), 10.08(1H, s).

(2) Preparation of 5-amino-N-[(4-aminophenyl)methyl]-1-naphthalenesulfonamide dihydrochloride.
Yield: %
$^1$H-NMR(DMSO-$d_6$, δ): 4.05(2H, d, J=6.0 Hz), 7.11(2H, d, J=8.7 Hz), 7.18(2H, d, J=8.4 Hz); 7.46(1H, d, J=6.9 Hz), 7.59-7.65(2H, m), 8.11(1H, d, J=7.2 Hz), 8.31-8.37(2H, m), 8.66(1H, t, J=6.0 Hz).

Example 46

Preparation of 5-amino-N-[[[3-(methylsulfonyl)amino]phenyl]methyl]-1-naphthalenesulfonamide hydrochloride (Compound No. 46)

(1) Preparation of N-[5-[[[[3-(methylsulfonyl)amino]phenyl]methyl]amino]sulfonyl]-1-naphthalenyl]acetamide.

N-[5-[[[(3-Aminophenyl) methyl]amino]sulfonyl]-1-naphthalenyl]acetamide (compound of Example 44(1): 120 mg, 0.32 mmol) was dissolved in tetrahydrofuran (5 ml), and then triethylamine (0.05 ml, 0.39 mmol) and methanesulfonyl chloride (0.030 ml, 0.39 mmol) were added, and the mixture was stirred at room temperature for 2 days. The reaction mixture was poured into diluted hydrochloric acid and extracted with ethyl acetate. The ethyl acetate layer was washed with saturated brine, and after the layer was dried over anhydrous sodium sulfate, the residue obtained by evaporation of the solvent under reduced pressure was purified by column chromatography on silica gel (eluent: hexane/ethyl acetate=1/3→ethyl acetate) to give the title compound as a light brown gummy substance (98.4 mg, 68.7%).

$^1$H-NMR(CD$_3$OD, δ): 2.29(3H, s), 2.83(3H, s), 4.04(2H, s), 6.81(1H, d, J=7.5 Hz), 6.95-6.97(2H, m), 7.01-7.06(1H, m), 7.57(1H, dd, J=8.7, 7.5 Hz), 7.63-7.69(2H, m), 8.19(1H, dd, J=7.5, 1.2 Hz), 8.23(1H, d, J=8.4 Hz), 8.57-8.64(1H, m).

(2) Preparation of 5-amino-N-[[[3-(methylsulfonyl)amino]phenyl]methyl]-1-naphthalenesulfonamide hydrochloride.
Yield: 81.1%
$^1$H-NMR(CD$_3$OD, δ): 2.87(3H, s), 4.10(2H, s), 6.79(1H, dt, J=7.2, 1.2 Hz), 6.93-6.96(2H, m), 7.02(1H, dd, J=8.7, 7.5 Hz), 7.68(1H, dd, J=7.5, 1.2 Hz), 7.75(2H, dd, J=8.4, 7.5 Hz), 8.18(1H, dt, J=8.7, 1.2 Hz), 8.31(1H, dd, J=7.2, 1.2 Hz), 8.80(1H, dd, J=8.4, 1.2 Hz).

Example 47

Preparation of 5-amino-N-[[4-(dimethylamino)phenyl]methyl)-1-naphthalenesulfonamide dihydrochloride (Compound No. 47)

(1) Preparation of N-[5-[[[[4-(dimethylamino)phenyl]methyl]amino]sulfonyl]-1-naphthalenyl]acetamide.
Yield: 79%
$^1$H-NMR(DMSO-$d_6$, δ): 2.20(3H, s), 2.81(6H, s), 3.89(2H, d, J=6.0 Hz), 6.55(2H, d, J=8.4 Hz), 6.95(2H, d, J=8.4 Hz), 7.64(1H, dd, J=8.4, 6.9 Hz), 7.67(1H, dd, J=8.4, 7.5 Hz), 7.76(1H, d, J=7.5 Hz), 8.13(1H, dd, J=7.5, 0.9 Hz), 8.32(1H, t, J=6.0 Hz), 8.33(1H, d, J=6.9 Hz), 8.53(1H, d, J=8.4 Hz), 10.06(1H, s), (2) Preparation of 5-amino-N-[[4-(dimethylamino)phenyl]methyl-1-naphthalenesulfonamide dihydrochloride.
Yield: 56%
$^1$H-NMR(DMSO-$d_6$, δ): 3.01(6H, s), 4.06(2H, d, J=6.0 Hz), 7.16(2H, d, J=8.4 Hz), 7.37(2H, d, J=8.4 Hz), 7.48(1H, d, J=7.5 Hz), 7.62(1H, dd, J=8.1, 7.8 Hz), 8.09(1H, d, J=7.5 Hz), 8.33(1H, d, J=8.4 Hz), 8.36(1H, d, J=8.4 Hz), 8.63(1H, t, J=6.0 Hz).

Example 48

Preparation of 4-[[[(5-amino-1-naphthalenyl)sulfonyl]-amino]methyl]benzoic acid hydrochloride
(Compound No. 48)

(1) Preparation of 4-[[[(5-acetamido-1-naphthalenyl)sulfonyl]amino]methyl]benzoic acid.

4-(Aminomethyl)benzoic acid (726 mg, 4.8 mmol) and triethylamine (0.67 ml, 4.8 mmol) were dissolved in a mixed solution of 2N sodium hydroxide solution (2.4 ml, 4.8 mmol), dioxane (4.8 ml) and water (12 ml). A suspension of N-[5-(chlorosulfonyl)-1-naphthalenyl]acetamide (1.135 g, 4 mmol) in dioxane (4 ml) and methanol (12 ml) was added to the mixture under ice cooling and stirring, and the mixture was stirred at room temperature for 30 minutes. The reaction mixture was poured into diluted hydrochloric acid, and the precipitated solid was washed with water and dried under reduced pressure to give the title compound as a light brown crystal (1,361 g, 85.4%).

$^1$H-NMR(DMSO-$d_6$, δ): 2.20(3H, s), 4.11(2H, d, J=6.0 Hz), 7.30(2H, d, J=8.1 Hz), 7.62-7.72(2H, m), 7.76-7.80(3H, m), 8.15(1H, dd, J=7.5, 0.9 Hz), 8.35(1H, d, J=8.4 Hz), 8.52 (1H, d, J=8.7 Hz), 8.66(1H, t, J=6.0 Hz), 10.08(1H, s).

(2) Preparation of 4-[[[(5-amino-1-naphthalenyl)sulfonyl]amino]methyl]benzoic acid hydrochloride.

Yield: 64.1%

$^1$H-NMR(CD$_3$OD, δ): 4.21(2H, s), 7.11(1H, d, J=8.7 Hz), 7.17(1H, d, J=8.7 Hz), 7.67-7.78)5H, m), 8.20(1H, ddt, J=8.7, 6.0, 1.2 Hz), 8.31(1H, ddd, J=7.2, 6.0, 1.2 Hz), 8.81(1H, dt, J=8.4, 1.2 Hz).

Example 49

Preparation of 5-amino-N-[[4-(methylsulfonyl)phenyl]methyl]-1-naphthalenesulfonamide hydrochloride (Compound No. 49)

(1) Preparation of N-[5-[[[[4-(methylsulfonyl)phenyl]methyl]amino]sulfonyl]-1-naphthalenyl]acetamide.

Yield: 91%

$^1$H-NMR(DMSO-$d_6$, δ): 2.20(3H, s), 3.14(3H, s), 4.15 (2H, d, J=6.0 Hz), 7.43(2H, d, J=8.1 Hz), 7.63(1H, dd, J=8.4, 8.1 Hz), 7.69(1H, dd, J=9.0, 8.1 Hz), 7.73(2H, d, J=8.1 Hz), 7.65(1H, dd, J=9.0, 8.4 Hz), 8.13(1H, d, J=7.2 Hz), 8.35(1H, d, J=8.4 Hz), 8.51(1H, d, J=8.4 Hz), 8.73(1H, t, J=6.0 Hz), 10.11(1H, s).

(2) Preparation of 5-amino-N-[[4-(methylsulfonyl)phenyl]methyl]-1-naphthalenesulfonamide hydrochloride.

Yield: 84%

$^1$H-NMR(DMSO-$d_6$, δ): 3.16(3H, s), 4.14(2H, d, J=6.3 Hz), 7.41(3H, d, J=8.1 Hz), 7.61(2H, dd, J=8.4, 7.5 Hz), 7.73(2H, d, J=8.1 Hz), 8.13(1H, d, J=6.9 Hz), 8.31(1H, d, J=8.4 Hz), 8.36(1H, d, J=8.4 Hz), 8.72(1H, t, J=6.3 Hz).

Example 50

Preparation of 5-amino-N-[[4-(sulfamoyl)phenyl] methyl]-1-naphthalenesulfonamide hydrochloride
(Compound No. 50)

(1) Preparation of N-[5-[[[[4-(sulfamoyl)phenyl]methyl] amino]sulfonyl]-1-naphthalenyl]acetamide.

Yield: 33.4%

$^1$H-NMR(DMSO-$d_6$, δ): 2.20(3H, s), 4.10(2H, d, J=6.3 Hz), 7.29(2H, s), 7.36(2H, d, J=8.1 Hz), 7.63-7.79(5H, m), 8.15(1H, dd, J=8.4, 0.9 Hz), 8.35(1H, d, J=8.1 Hz), 8.52(1H, d, J=8.7 Hz), 8.66(1H, t, J=6.3 Hz), 10.08(1H, s).

(2) Preparation of 5-amino-N-[[4-(sulfamoyl)phenyl]methyl]-1-naphthalenesulfonamide hydrochloride.

Yield: 53.1%

$^1$H-NMR(DMSO-$d_6$, δ): 4.09(2H, d, J=6.6 Hz), 7.33-7.35 (5H, m), 7.57-7.67(4H, m), 8.13(1H, d, J=7.5 Hz), 8.29(1H, d, J=8.1 Hz), 8.36(1H, d, J=8.7 Hz), 8.64(1H, t, J=6.3 Hz).

Example 51

Preparation of 5-amino-N-(2-furanylmethyl)-1-naphthalenesulfonamide hydrochloride
(Compound No. 51)

(1) Preparation of N-[5-[[(2-furanylmethyl)amino]sulfonyl]-1-naphthalenyl]acetamide.

Yield: 87.9%

$^1$H-NMR(DMSO-$d_6$, δ): 2.19(3H, s), 4.06(2H, d, J=6.0 Hz), 6.03(1H, d, J=3.0 Hz), 6.20(1H, dd, J=3.0, 1.8 Hz), 7.36(1H, dd, J=1.8, 0.9 Hz), 7.60-7.68(2H, m), 7.74(1H, d, J=7.2 Hz), 8.10(1H, dd, J=7.5, 1.2 Hz), 8.32(1H, d, J=8.7 Hz), 8.48(1H, d, J=8.4 Hz), 8.54(1H, t, J=6.0 Hz), 10.06(1H, s).

(2) Preparation of 5-amino-N-(2-furanylmethyl)-1-naphthalenesulfonamide hydrochloride.

N-[5-[[(2-furanylmethyl)amino]sulfonyl]-1-naphthalenyl]acetamide (202 mg, 0.59 mmol) was suspended in a solution of sodium hydroxide (148 mg, 3.7 mmol) in 1-propanol (4 ml), and the mixture was refluxed for 5 hours. After the reaction mixture was concentrated, saturated brine was added and the mixture was extracted with ethyl acetate. The ethyl acetate layer was washed with saturated brine, and after the layer was dried over anhydrous sodium sulfate, the residue obtained by evaporation of the solvent under reduced pressure was purified by column chromatography on silica gel (eluent: ethyl acetate) to give a brown oil. This oil was dissolved in 1-propanol (1 ml), 2N hydrochloric acid (0.4 ml) was added thereto, and the mixture was stirred at room temperature for 20 minutes. The precipitated crystal was filtered, washed with 1-propanol and diisopropyl ether, and dried under vacuum to give the title compound as an ash white crystal (135 mg, 67.8%).

$^1$H-NMR(DMSO-$d_6$, δ): 4.05(2H, d, J=5.7 Hz), 6.01(1H, d, J=3.3 Hz), 6.20(1H, dd, J=3.3, 1.5 Hz), 7.34-7.35(1H, m), 7.43(1H, d, J=7.5 Hz), 7.57-7.68(2H, m), 8.11(1H, d, J=7.2 Hz), 8.34(2H, d, J=8.7 Hz), 8.55(1H, t, J=5.7 Hz).

Example 52

Preparation of 5-amino-N-[(5-methyl-2-furanyl)methyl]-1-naphthalenesulfonamide hydrochloride
(Compound No. 52)

(1). Preparation of N-[5-[[[(5-methyl-2-furanyl)methyl] amino-]sulfonyl]-1-naphthalenyl]acetamide.

Yield: 87.6%

$^1$H-NMR(DMSO-$d_6$, δ): 1.90(3H, s), 2.19(3H, s), 4.00 (2H, d, J=5.7 Hz), 5.71-5.72(1H, m), 5.86(1H, d, J=3.0 Hz), 7.58-7.68(2H, m), 7.74(1H, d, J=6.9 Hz), 8.08(1H, dd, J=7.2, 0.9 Hz), 8.31(1H, d, J=8.4 Hz), 8.47(1H, d, J=9.0 Hz), 8.49 (1H, t, J=5.7 Hz), 10.06(1H, s).

(2) Preparation of 5-amino-N-[(5-methyl-2-furanyl)methyl]-1-naphthalenesulfonamide hydrochloride.

Preparation was carried out in the same manner as the method of Example 51(2).

Yield: 70.8%

$^1$H-NMR(CD$_3$OD, δ): 1.81(3H, m), 4.10(2H, s), 5.51-5.52 (1H, m), 5.68(1H, d, J=3.0 Hz), 7.67-7.79(3H, m), 8.18(1H, dt, J=8.4, 1.2 Hz), 8.29(1H, dd, J=7.5, 1.2 Hz), 8.78(1H, dt, J=8.1, 1.2 Hz).

Example 53

Preparation of 5-amino-N-(2-pyridinylmethyl)-1-naphthalenesulfonamide dihydrochloride
(Compound No. 53)

(1) Preparation of N-[5-[[(2-pyridinylmethyl)amino]sulfonyl]-1-naphthalenyl]acetamide.

Yield: 95.4%

$^1$H-NMR(DMSO-d$_6$, δ): 2.20(3H, s), 4.13(2H, d, J=6.0 Hz), 7.13-7.17(1H, m), 7.24(1H, d, J=7.8 Hz), 7.57-7.71(3H, m), 7.76(1H, d, J=7.5 Hz), 8.13(1H, dd, J=7.2, 1.2 Hz), 8.30-8.34(2H, m), 8.53(1H, d, J=8.1 Hz), 8.66(1H, t, J=6.0 Hz), 10.06(1H, s).

(2) Preparation of 5-amino-N-(2-pyridinylmethyl)-1-naphthalenesulfonamide dihydrochloride.

Yield: 82.6%

$^1$H-NMR(DMSO-d$_6$, δ): 4.41(2H, d, J=6.0 Hz), 7.46(1H, d, J=7.5 Hz), 7.61-7.69(4H, m), 8.15-8.21(2H, m), 8.32(1H, d, J=8.7 Hz), 8.36(1H, d, J=8.7 Hz), 8.57(1H, dd, J=6.0, 1.5 Hz), 9.05(1H, t, J=6.0 Hz).

Example 54

Preparation of 5-amino-N-[(1H-benzimidazol-2-yl)methyl]-1-naphthalenesulfonamide dihydrochloride
(Compound No. 54)

(1) Preparation of N-[5[[[(1H-benzimidazol-2-yl)methyl]amino]sulfonyl]-1-naphthalenyl]acetamide.

Yield: 58.0%

$^1$H-NMR(DMSO-d$_6$, δ): 2.20(3H, s), 4.21(2H, d, J=6.0 Hz), 7.12-7.18(2H, m), 7.45-7.50(2H, m), 7.66(1H, t, J=8.4 Hz), 7.76(1H, d, J=7.8 Hz), 8.19(1H, dd, J=7.5, 1.2 Hz), 8.35(1H, d, J=8.4 Hz), 8.54(1H, d, J=8.4 Hz), 8.74(1H, t, J=6.0 Hz), 10.08(1 H, s), 12.41(1H, br).

(2) Preparation of 5-amino-N-[(1H-benzimidazol-2-yl)methyl]-1-naphthalenesulfonamide dihydrochloride.

Yield: 73.1%

$^1$H-NMR(CD$_3$OD, δ): 4.85(2H, s), 7.58-7.64(2H, m), 7.68-7.83(5H, m), 8.30(1H, dt, J=8.7, 1.2 Hz), 8.38(1H, dd, J=7.5, 1.2 Hz), 8.76(1H, dt, J=9.0, 1.2 Hz).

Example 55

Preparation of 5-amino-N-(1-phenylethyl)-1-naphthalenesulfonamide
(Compound No. 55)

(1) Preparation of N-[5-[[(1-phenylethyl)amino]sulfonyl]-1-naphthalenyl]acetamide.

Yield: 67.9%

$^1$H-NMR(DMSO-d$_6$, δ): 1.15(3H, d, J=6.9 Hz), 2.19(3H, s), 4.32(1H, m), 7.03-7.10(5H, m), 7.54(1H, dd, J=8.4, 7.2 Hz), 7.65(1H, dd, J=8.4, 7.8 Hz), 7.46(1H, d, J=6.9 Hz), 8.04(1H, dd, J=7.2, 0.9 Hz), 8.26(1H, d, J=8.4 Hz), 8.50(1H, dd, J=8.4, 5.1 Hz), 10.01(1H, s).

(2) Preparation of 5-amino-N-(1-phenylethyl)-1-naphthalenesulfonamide.

Preparation was carried out in the same manner as the method of Example 1(2). (However the compound was isolated as a free form without converting to hydrochloride.)

Yield: 27.9%

$^1$H-NMR(DMSO-d$_6$, δ): 1.11(3H, d, J=6.6 Hz), 4.29(1H, m), 6.79(1H, d, J=7.5 Hz), 7.07-7.16(5H, m), 7.36(2H, m), 7.85(1H, d, J=8.4 Hz), 7.99(1H, dd, J=7.2, 0.9 Hz), 8.27-8.31 (2H, m).

Example 56

Preparation of 5-amino-N-[1-(1-naphthalenyl)ethyl]-1-naphthalenesulfonamide hydrochloride
(Compound No. 56)

(1) Preparation of N-[5-[[[1-(1-naphthalenyl)ethyl]amino]sulfonyl]-1-naphthalenyl]acetamide.

Yield. 71.0%

$^1$H-NMR(DMSO-d$_6$, δ): 1.29(3H, d, J=6.9 Hz), 5.19(1H, m), 7.17(1H, d, J=7.5 Hz), 7.38-7.46(4H, m), 7.62-7.69(2H, m), 7.50(1H, d, J=7.5 Hz), 7.81-7.84(1H, m), 7.94-8.00(2H, m), 8.20(1H, d, J=8.4 Hz), 8.56(1H, d, J=8.4 Hz), 8.70(1H, d, J=8.1 Hz), 9.99(1H, s).

(2) Preparation of 5-amino-N-[1-(1-naphthalenyl)ethyl]-1-naphthalenesulfonamide hydrochloride.

Yield: 80.2%

$^1$H-NMR(DMSO-d$_6$, δ): 1.29(3H, d, J=6.6 Hz), 5.18(1H, m), 7.17(1H, t, J=7.5 Hz), 7.36-7.46(5H, m), 7.57(1H, t, J=7.8 Hz), 7.81-7.84(1H, m), 7.93-7.96(1H, m), 7.99(1H, d, J=7.5 Hz), 8.20(1H, d, J=8.7 Hz), 8.38(1H, d, J=8.7 Hz), 8.70(1H, d, J=8.1 Hz).

Example 57

Preparation of 5-amino-N-(2,3-dihydro-1H-inden-1-yl)-1-naphthalenesulfonamide (Compound No. 57)

(1) Preparation of N-[5-[[(2,3-dihydro-1H-inden-1-yl)amino]sulfonyl]-1-naphthalenyl]acetamide.

Yield: 91.8%

$^1$H-NMR(DMSO-d$_6$, δ): 1.49-1.62(1H, m), 1.88-1.97(1H, m), 2.21(3H, s), 2.53-2.64(1H, m), 2.71-2.29(1H, m), 4.65 (1H, q, J=8.1 Hz), 6.90(1H, d, J=7.5 Hz), 7.03-7.08(1H, m), 7.12-7.16(2H, m), 7.66-7.72(2H, m), 7.79(1H, d, J=7.2 Hz), 8.27(1H, dd, J=8.4, 0.9 Hz), 8.39(1H, d, J=8.7 Hz), 8.51(1H, d, J=9.0 Hz), 8.57(1H, d, J=8.4 Hz), 10.09(1H, s).

(2) Preparation of 5-amino-N-(2,3-dihydro-1H-inden-1-yl)-1-naphthalenesulfonamide.

Preparation was carried out in the same manner as the method of Example 51(2), provided that the compound was isolated as a free form without being converting to hydrochloride.

Yield: 63.9%

$^1$H-NMR(DMSO-d$_6$, δ): 1.50-1.63(1H, m), 1.87-1.97(1H, m), 2.59(1H, q, J=8.4 Hz), 2.74(1H, ddd, J=15.9, 8.7, 3.0 Hz), 4.59(1H, q, J=8.4 Hz), 5.99(2H, s), 6.81(1H, d, J=7.8 Hz), 6.91(1H, d, J=7.2 Hz), 7.02-7.07(1H, m), 7.11-7.15(2H, m), 7.37(1H, dd, J=8.4, 7.8 Hz), 7.48(1H, dd, J=8.1, 7.5 Hz), 7.88(1H, d, J=8.4 Hz), 8.16(1H, dd, J=7.2, 0.9 Hz), 8.82(1H, d, J=8.7 Hz), 8.41(1H, d, J=8.4 Hz).

Example 58

Preparation of 5-amino-N-(1,2,3,4-tetrahydro-1-naphthalenyl)-1-naphthalenesulfonamide (Compound No. 58)

(1) Preparation of N-[5-[[(1,2,3,4-tetrahydro-1-naphthalenyl)amino]sulfonyl]-1-naphthalenyl]acetamide.
Yield: 93.8%
$^1$H-NMR(DMSO-$d_6$, δ): 1.42-1.50(3H, m), 1.66-1.76(1H, m), 2.21(3H, s), 2.54-2.66(2H, m), 4.26-4.33(1H, m), 6.90-7.02(3H, m), 7.06-7.11(1H, m), 7.63-7.72(2H, m), 7.79(1H, d, J=7.5 Hz), 8.28(1H, dd, J=7.5, 1.2 Hz), 8.39(1H, d, J=8.7 Hz), 8.45(1H, d, J=9.0 Hz), 8.55(1H, d, J=8.4 Hz), 10.09(1H, s).

(2) Preparation of 5-amino-N-(1,2,3,4-tetrahydro-1-naphthalenyl)-1-naphthalenesulfonamide.
Preparation was carried out in the same manner as the method of Example 51(2). (However the compound was isolated as a free form without converting to hydrochloride.)
Yield: 84.4%
$^1$H-NMR(DMSO-$d_6$, δ): 1.44(3H, brs), 1.65-1.76(1H, m), 2.54-2.65(2H, m), 4.23(1H, q, J=9.0 Hz), 5.98(2H, s), 6.81(1H, d, J=7.2 Hz), 6.92-7.10(4H, m), 7.35(1H, dd, J=8.4, 7.8 Hz), 7.48(1H, dd, J=8.4, 7.5 Hz), 7.86(1H, d, J=8.4 Hz), 8.17(1H, dd, J=7.5, 1.2 Hz), 8.25(1H, d, J=8.7 Hz), 8.41(1H, d, J=8.7 Hz).

Example 59

Preparation of 5-amino-N-(2-phenylpropyl)-1-naphthalenesulfonamide (Compound No. 59)

(1) Preparation of N-[5-[[(2-phenylpropyl)amino]sulfonyl]-1-naphthalenyl]acetamide.
Yield: 70%
$^1$H-NMR(DMSO-$d_6$, δ): 1.43(6H, s), 2.20(3H, s), 7.04(3H, m), 7.21(2H, m), 7.49(1H, dd, J=8.4, 7.5 Hz), 7.66(1H, dd, J=8.4, 7.5 Hz), 7.46(1H, d, J=7.5 Hz), 7.88(1H, dd, J=7.2, 1.2 Hz), 8.25(1H, d, J=8.4 Hz), 8.35(1H, s), 8.56(1H, d, J=8.4 Hz), 10.02(1H, s).

(2) Preparation of 5-amino-N-(2-phenylpropyl)-1-naphthalenesulfonamide.
Preparation was carried out in the same manner as the method of Example 51(2). (However the compound was isolated as a free form without converting to hydrochloride.)
Yield: 79%
$^1$H-NMR(DMSO-$d_6$, δ): 1.39(6H, s), 5.92(2H, brs), 6.78(1H, d, J=7.5 Hz), 7.08(3H, m), 7.25(2H, m), 7.31(1H, dd, J=8.4, 8.1 Hz), 7.35(1H, dd, J=8.1, 7.8 Hz), 7.83(1H, d, J=7.5 Hz), 7.87(1H, d, J=8.4 Hz), 8.15(1H, s), 8.29(1H, d, J=8.4 Hz).

Example 60

Preparation of 5-amino-N-methyl-N-(phenylmethyl)-1-naphthalenesulfonamide hydrochloride (Compound No. 60)

(1) Preparation of N-[5-[[[N-methyl-N-(phenylmethyl)]amino]sulfonyl]-1-naphthalenyl]acetamide.
Yield: 80%
$^1$H-NMR(DMSO-$d_6$, δ): 2.21(3H, s), 2.70(3H, d, J=0.9 Hz), 4.40(2H, s), 7.32(5H, m), 7.73(3H, m), 8.19(1H, dd, J=7.5, 1.2 Hz), 8.41(1H, dd, J=8.4, 0.9 Hz), 8.52(1H, d, J=8.1 Hz), 10.11(1H, s).

(2) Preparation of 5-amino-N-methyl-N-(phenylmethyl)-1-naphthalenesulfonamide hydrochloride.
Yield: 86%
$^1$H-NMR(DMSO-$d_6$, δ): 2.68(3H, s), 4.38(2H, s), 7.31(5H, m), 7.39(1H, d, J=8.1 Hz), 7.62(1H, dd, J=8.4, 7.8 Hz), 7.71(1H, dd, J=8.1, 7.8 Hz), 8.19(1H, d, J=7.2 Hz), 8.30(1H, d, J=8.4 Hz), 8.44(1H, d, J=8.4 Hz).

Example 61

Preparation of 2-[(5-amino-1-naphthalenyl)sulfonyl]-2,3-dihydro-1H-isoindole hydrochloride (Compound No. 61)

(1) Preparation of N-[5-[(2,3-dihydro-1H-isoindol-2-yl)sulfonyl]-1-naphthalenyl]acetamide.
Yield: 88.7%
$^1$H-NMR(DMSO-$d_6$, δ): 2.19(3H, s), 4.69(4H, s), 7.25-7.31(4H, m), 7.68-7.78(3H, m), 8.15(1H, d, J=7.2 Hz), 8.40(1H, d, J=8.4 Hz), 8.60(1H, d, J=8.1 Hz), 10.09(1H, s).

(2) Preparation of 2-[(5-amino-1-naphthalenyl)sulfonyl]-2,3-dihydro-1H-isoindole hydrochloride.
Yield: 86.3%
$^1$H-NMR(CD$_3$OD, δ): 4.73(4H, s), 7.21-7.27(4H, m), 7.72-7.83(2H, m), 7.86(1H, dd, J=8.7, 7.5 Hz), 8.28(1H, dt, J=8.4, 1.2 Hz), 8.35(1H, dd, J=7.2, 0.9 Hz), 9.02(1H, dt, J=8.4, 0.9 Hz).

Example 62

Preparation of 2-[(5-amino-1-naphthalenyl)sulfonyl]-1,2,3,4-tetrahydroisoquinoline hydrochloride (Compound No. 62)

(1) Preparation of N-[5-[(1,2,3,4-tetrahydroisoquinolin-2-yl)sulfonyl]-1-naphthalenyl]acetamide.
Yield: 70.1%
$^1$H-NMR(DMSO-$d_6$, δ): 2.19(3H, s), 2.82(2H, t, J=5.7 Hz), 3.54(2H, t, J=5.7 Hz), 4.41(2H, s), 7.09(4H, m), 7.66-7.76(3H, m), 8.25(1H, dd, J=7.2, 0.9 Hz), 8.40(1H, d, J=8.7 Hz), 8.50(1H, d, J=8.4 Hz), 10.08(1H, s).

(2) Preparation of 2-[(5-amino-1-naphthalenyl)sulfonyl]-1,2,3,4-tetrahydroisoquinoline hydrochloride.
Yield: 69.9%
$^1$H-NMR(DMSO-$d_6$, δ): 2.81(2H, t, J=5.7 Hz), 3.53(2H, t, J=6.0 Hz), 4.39(2H, s), 7.08-7.14(4H, m), 7.86(1H, d, J=7.5 Hz), 7.60(1H, t, J=7.8 Hz), 7.71(1H, t, J=7.8 Hz), 8.23-8.30(2H, m), 8.43(1H, d, J=8.4 Hz).

Example 63

Preparation of 5-amino-N-cyclohexylmethyl-1-naphthalenesulfonamide hydrochloride (Compound No. 63)

(1) Preparation of N-[5-[[(cyclohexylmethyl)amino]sulfonyl]-1-naphthalenyl]acetamide.
Yield: 95%

$^1$H-NMR(DMSO-d$_6$, δ): 0.72(2H, m), 1.01(3H, m), 1.24 (1H, m), 1.53(5H, m), 2.19(3H, s), 2.61(2H, t, J=6.3 Hz), 7.66(2H, ddd, J=8.7, 7.2, 1.5 Hz), 7.75(1H, d, J=7.2 Hz), 7.93(1H, t, J=6.0 Hz), 8.12(1H, dd, J=7.2, 0.9 Hz), 8.34(1H, d, J=8.7 Hz), 8.52(1H, d, J=8.4 Hz), 10.06(1H, s).

(2) Preparation of 5-amino-N-cyclohexylmethyl-1-naphthalenesulfonamide hydrochloride.

Yield: 91%

$^1$H-NMR(DMSO-d$_6$, δ): 0.72(2H, m), 1.02(3H, m), 1.25 (1H, m), 1.53(5H, m), 2.60(2H, t, J=6.3 Hz), 7.43(1H, d, J=7.5 Hz), 7.61(1H, dd, J=8.1, 8.1 Hz), 7.68(1H, dd, J=8.4, 7.5 Hz), 7.94(1H, t, J=5.7 Hz), 8.13(1H, d, J=7.5 Hz), 8.36 (1H, d, J=8.4 Hz), 8.37(1H, d, J=8.1 Hz).

Example 64

Preparation of
5-amino-N-phenyl-1-naphthalenesulfonamide
hydrochloride (Compound No. 64)

(1) Preparation of N-[5-[(phenylamino)sulfonyl]-1-naphthalenyl]acetamide.

Yield: 58.4%

$^1$H-NMR(DMSO-d$_6$, δ): 2.17(3H, s), 6.89-6.96(1H, m), 6.99-7.03(2H, m), 7.11-7.14(2H, m), 7.63(1H, dd, J=8.4, 7.5 Hz), 7.67-7.72(1H, m), 7.76(1H, dd, J=6.9 Hz), 8.22(1H, dd, J=7.2, 0.9 Hz), 8.32(1H, d, J=8.4 Hz), 8.58(1H, d, J=8.4 Hz), 10.03(1H, s), 10.67(1H, s).

(2) Preparation of 5-amino-N-phenyl-1-naphthalenesulfonamide hydrochloride.

Yield: 85.7%

$^1$H-NMR(CD$_3$OD, δ): 6.91-6.99(3H, m), 7.05-7.11(2H, m), 7.69-7.80(3H, m), 8.19(1H, dt, J=8.4, 1.2 Hz), 8.36(1H, dd, J=7.5, 1.2 Hz), 8.90(1H, dt, J=8.4, 1.2 Hz).

Example 65

Preparation of
5-amino-N-(2-phenylethyl)-1-naphthalenesulfonamide
hydrochloride (Compound No. 65)

(1) Preparation of N-[5-[[(2-phenylethyl)amino]sulfonyl]-1-naphthalenyl]acetamide.

Yield: 83.6%

$^1$H-NMR(DMSO-d$_6$, δ): 2.19(3H, s), 2.61(2H, t, J=7.8 Hz), 2.98-3.05(2H, m), 7.03-7.05(2H, m), 7.10-7.21(3H, m), 7.63-7.69(2H, m), 7.75(1H, d, J=6.9 Hz), 8.10(1H, t, J=5.7 Hz), 8.12(1H, t, J=7.5 Hz), 8.34(1H, d, J=8.7 Hz), 8.49(1H, d, J=8.4 Hz), 10.07(1H, s).

(2) Preparation of 5-amino-N-(2-phenylethyl)-1-naphthalenesulfonamide hydrochloride.

Yield: 92.5%

$^1$H-NMR(CD$_3$OD, δ): 2.61(2H, t, J=7.2 Hz), 3.14(2H, t, J=7.2 Hz), 6.91-6.94(2H, m), 7.01-7.10(3H, m), 7.64-7.68 (1H, m), 7.71(1H, t, J=7.5 Hz), 7.79(1H, dd, J=8.4, 7.5 Hz), 8.22(1H, dt), J=8.7, 0.9 Hz), 8.33(1H, dd, J=7.5, 1.2 Hz), 8.72(1H, d, J=8.4 Hz).

TEST EXAMPLE

By using the compounds synthesized above, effects on proliferation of Jurkat cells by sole administration and inhibitory effects on cell proliferation by administration in combination with bleomycin were examined. Materials and methods are as follows. Jurkat cells obtained from Dainippon Pharmaceutical Co. Ltd. were inoculated at about 10,000 cells per well in a 96 well culture plate, and incubated in 10% bovine fetal serum (Irvine Scientific) supplemented with RPMI1640(ICN) medium in 5% CO$_2$ incubator at 37° C. For the culture, each compound was added alone, or the culture was further added with bleomycin (Wako) to give a concentration of 5 μg/ml or 10 μg/ml. 36 hours after the incubation, the number of living cells was counted by the MTS method.

More specifically, 20 μl of CellTiter96™ AQueous One Solution (Promega) was added per one well, and after the cells were incubated for additional one hour, an absorbance at 490 nm was measured by using a microplate reader. The same culture added with DMSO as a solvent at final concentration of 0.25% was used as a control. The number of cells in the control was considered as 100% survival rate, and for each compound, survival rates by sole administration or a combined administration were calculated. Treatments solely with bleomycin at 5 μg/ml or 10 μg/ml gave about 5 to 10% of decrease in the survival rates of the Jurkat cells. Whilst, when the compound of the present invention coexisted, the survival rates of the Jurkat cells by bleomycin at 5 μg/ml or 10 μg/ml were remarkably decreased. The results are shown in the following table. In the table, ++ indicates observation of remarkable enhancement, and + indicates moderated enhancement.

| Compound Number | Activity |
|---|---|
| 1 | + |
| 3 | + |
| 5 | + |
| 6 | ++ |
| 9 | + |
| 12 | ++ |
| 14 | + |
| 15 | + |
| 18 | ++ |
| 19 | ++ |
| 21 | ++ |
| 23 | + |
| 24 | ++ |
| 25 | ++ |
| 26 | + |
| 28 | ++ |
| 31 | ++ |
| 35 | + |
| 36 | + |
| 38 | + |
| 41 | ++ |
| 42 | ++ |
| 43 | + |
| 44 | + |
| 48 | + |
| 53 | + |
| 55 | + |
| 56 | + |
| 58 | + |
| 64 | + |

INDUSTRIAL APPLICABILITY

The medicaments of the present invention enhance the effect of a cancer therapy based on the mode of action of DNA injury and reduce a dose of an anticancer agent and/or radiation. Therefore, the medicaments can reduce side effects resulting from the cancer therapy.

What is claimed is:

1. A compound represented by the general formula (II) or a salt thereof:

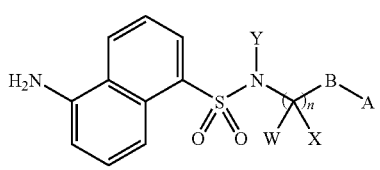

(II)

wherein A represents a $C_6$ to $C_{10}$ aryl group which may be substituted, or a 4 to 10-membered monocyclic or bicyclic and unsaturated, partly saturated, or completely saturated heterocyclic group which may be substituted, wherein said heterocyclic group comprises 1 to 4 hetero atoms selected from the group consisting of nitrogen atom, oxygen atom, and sulfur atom; B represents a single bond or a methylene group which may be substituted; and W and X independently represent a hydrogen atom or a $C_1$ to $C_6$ alkyl group which may be substituted, or W may combine with a substituent of A to represent a $C_1$ to $C_4$ alkylene group wherein said alkylene group may be substituted; Y represents a hydrogen atom or a $C_1$ to $C_6$ alkyl group which may be substituted, or Y may combine with a substituent of A to represent a $C_1$ to $C_4$ alkylene group wherein said alkylene group may be substituted; and n represents 1; provided that the following compound is excluded:

5-amino-N-(phenylmethyl)-1-naphthalenesulfonamide.

2. A medicament composition which comprises as an active ingredient a compound represented by the general formula (II) or a physiologically acceptable salt thereof,

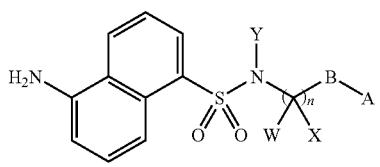

(II)

wherein A represents a $C_3$ to $C_6$ cycloalkyl group which may be substituted, a $C_6$ to $C_{10}$ aryl group which may be substituted, or a 4 to 10-membered monocyclic or bicyclic and unsaturated, partly saturated, or completely saturated heterocyclic group which may be substituted, wherein said heterocyclic group comprises 1 to 4 hetero atoms selected from the group consisting of nitrogen atom, oxygen atom, and sulfur atom; B represents a single bond or a methylene group which may be substituted; and W and X independently represent a hydrogen atom or a $C_1$ to $C_6$ alkyl group which may be substituted, or W may combine with a substituent of A to represent a $C_1$ to $C_4$ alkylene group wherein said alkylene group may be substituted; Y represents a hydrogen atom or a $C_1$ to $C_6$ alkyl group which may be substituted, or Y may combine with a substituent of A to represent a $C_1$ to $C_4$ alkylene group wherein said alkylene group may be substituted; and n represents 1; the medicament composition further comprising at least one pharmaceutically acceptable additive.

3. A medicament composition according to claim 2, which is used for enhancing an effect of a cancer therapy based on a mode of action of DNA injury.

4. The compound or a salt thereof according to claim 1, wherein B is a single bond.

5. The compound or a salt thereof according to claim 1, wherein the compound represented by the aforementioned general formula (II) is a compound selected from the group consisting of the following compounds:

5-amino-N-[(1-naphthalenyl)methyl]-1-naphthalenesulfonamide;
5-amino-N-[(2-naphthalenyl)methyl]-1-naphthalenesulfonamide;
5-amino-N-[(2-chlorophenyl)methyl]-1-naphthalenesulfonamide;
5-amino-N-[(3-chlorophenyl)methyl]-1-naphthalenesulfonamide;
5-amino-N-[(4-chlorophenyl)methyl]-1-naphthalenesulfonamide;
5-amino-N-[(2,4-dichlorophenyl)methyl]-1-naphthalenesulfonamide;
5-amino-N-[(3,4-dichlorophenyl)methyl]-1-naphthalenesulfonamide;
5-amino-N-[(3,5-dichlorophenyl)methyl]-1-naphthalenesulfonamide;
5-amino-N-[(2-fluorophenyl)methyl]-1-naphthalenesulfonamide;
5-amino-N-[(3-fluorophenyl)methyl]-1-naphthalenesulfonamide;
5-amino-N-[(4-fluorophenyl)methyl]-1-naphthalenesulfonamide;
5-amino-N-[(2,6-difluorophenyl)methyl]-1-naphthalenesulfonamide;
5-amino-N-[(3,4-difluorophenyl)methyl]-1-naphthalenesulfonamide;
5-amino-N-[(3,5-difluorophenyl)methyl]-1-naphthalenesulfonamide;
5-amino-N-[(2-methylphenyl)methyl]-1-naphthalenesulfonamide;
5-amino-N-[(3-methylphenyl)methyl]-1-naphthalenesulfonamide;
5-amino-N-[(4-methylphenyl)methyl]-1-naphthalenesulfonamide;
5-amino-N-[[4-(1,1-dimethylethyl)phenyl]methyl]-1-naphthalenesulfonamide;
5-amino-N-[[2-(trifluoromethyl)phenyl]methyl]-1-naphthalenesulfonamide;
5-amino-N-[[3-(trifluoromethyl)phenyl]methyl]-1-naphthalenesulfonamide;
5-amino-N-[[4-(trifluoromethyl)phenyl]methyl]-1-naphthalenesulfonamide
5-amino-N-[[[1,1'-biphenyl]-4-yl]methyl]-1-naphthalenesulfonamide;
5-amino-N-[[[4'-methyl-1,1'-biphenyl]-2-yl]methyl]-1-naphthalenesulfonamide;
5-amino-N-[(2-methoxyphenyl)methyl]-1-naphthalenesulfonamide;
5-amino-N-[(3-methoxyphenyl)methyl]-1-naphthalenesulfonamide;
5-amino-N-[(4-methoxyphenyl)methyl]-1-naphthalenesulfonamide;
5-amino-N-[(3,4-methylenedioxyphenyl)methyl]-1-naphthalenesulfonamide;
5-amino-N-[(2,3-dimethoxyphenyl)methyl]-1-naphthalenesulfonamide;
5-amino-N-[(2,4-dimethoxyphenyl)methyl]-1-naphthalenesulfonamide;

5-amino-N-[(3,4-dimethoxyphenyl)methyl]-1-naphthalenesulfonamide;
5-amino-N-[(3,5-dimethoxyphenyl)methyl]-1-naphthalenesulfonamide;
5-amino-N-[(2,4,6-trimethoxyphenyl)methyl]-1-naphthalenesulfonamide;
5-amino-N-[(3,4,5-trimethoxyphenyl)methyl]-1-naphthalenesulfonamide;
5-amino-N-[(2-ethoxyphenyl)methyl]-1-naphthalenesulfonamide;
5-amino-N-[[3-(phenylmethoxy)phenyl]methyl]-1-naphthalenesulfonamide;
5-amino-N-[[4-(phenylmethoxy)phenyl]methyl]-1-naphthalenesulfonamide;
5-amino-N-[(6-methoxy-2-naphthalenyl)methyl]-1-naphthalenesulfonamide;
5-amino-N-[(3-hydroxyphenyl)methyl]-1-naphthalenesulfonamide;
5-amino-N-[(3,4-dihydroxyphenyl)methyl]-1-naphthalenesulfonamide;
5-amino-N-[(4-hydroxy-3-methoxyphenyl)methyl]-1-naphthalenesulfonamide;
5-amino-N-[(3-nitrophenyl)methyl]-1-naphthalenesulfonamide;
5-amino-N-[(4-nitrophenyl)methyl]-1-naphthalenesulfonamide;
5-amino-N-[(2-aminophenyl)methyl]-1-naphthalenesulfonamide;
5-amino-N-[(3-aminophenyl)methyl]-1-naphthalenesulfonamide;
5-amino-N-[(4-aminophenyl)methyl]-1-naphthalenesulfonamide;
5-amino-N-[[[3-(methylsulfonyl)amino]phenyl]methyl]-1-naphthalenesulfonamide;
5-amino-N-[[4-(dimethylamino)phenyl]methyl]-1-naphthalenesulfonamide;
4-[[[(5-amino-1-naphthalenyl)sulfonyl]amino]methyl] benzoic acid;
5-amino-N-[[4-(methylsulfonyl)phenyl]methyl]-1-naphthalenesulfonamide;
5-amino-N-[[4-(sulfamoyl)phenyl]methyl]-1-naphthalenesulfonamide;
5-amino-N-(2-furanylmethyl)-1-naphthalenesulfonamide;
5-amino-N-[(5-methyl-2-furanyl)methyl]-1-naphthalenesulfonamide;
5-amino-N-(2-pyridinylmethyl)-1-naphthalenesulfonamide;
5-amino-N-[(1H-benzimidazol-2-yl)methyl]-1-naphthalenesulfonamide;
5-amino-N-(1-phenylethyl)-1-naphthalenesulfonamide;
5-amino-N-[1-(1-naphthalenyl)ethyl]-1-naphthalenesulfonamide;
5-amino-N-(2,3-dihydro-1H-inden-1-yl)-1-naphthalenesulfonamide;
5-amino-N-(1,2,3,4-tetrahydro-1-naphthalenyl)-1-naphthalenesulfonamide;
5-amino-N-(2-phenylpropyl)-1-naphthalenesulfonamide;
5-amino-N-methyl-N-phenylmethyl)-1-naphthalenesulfonamide;
2-[(5-amino-1-naphthalenyl)sulfonyl]-2,3-dihydro-1H-isoindole;
2-[(5-amino-1-naphthalenyl)sulfonyl]-1,2,3,4-tetrahydroisoquinoline; and
5-amino-N-(2-phenylethyl)-1-naphthalenesulfonamide.

6. The medicament composition according to claim 3, wherein the cancer therapy based on the mode of action of DNA injury is carried out by the administration of an anticancer agent and/or radiation.

7. The medicament composition according to claim 6, wherein the anticancer agent is selected from the group consisting of bleomycin, adriamycin, cisplatin, cyclophosphamide, mitomycin C, and a derivative thereof.

8. The medicament composition according to claim 2, which is a specific inhibitor of a protein kinase 1 and/or an analogous enzyme thereof.

9. The medicament composition according to claim 2, which is used for reducing a side effect resulting from a cancer therapy based on the mode of action of DNA injury.

* * * * *